United States Patent [19]
Unger

[11] Patent Number: 5,874,062
[45] Date of Patent: Feb. 23, 1999

[54] METHODS OF COMPUTED TOMOGRAPHY USING PERFLUOROCARBON GASEOUS FILLED MICROSPHERES AS CONTRAST AGENTS

[75] Inventor: Evan C. Unger, Tucson, Ariz.

[73] Assignee: ImaRx Pharmaceutical Corp., Tucson, Ariz.

[21] Appl. No.: 445,299

[22] Filed: May 19, 1995

Related U.S. Application Data

[63] Continuation-in-part of Ser. No. 247,656, May 23, 1994, abandoned, and Ser. No. 116,982, Sep. 7, 1993, Pat. No. 5,456,900, which is a division of Ser. No. 980,594, Jan. 19, 1993, Pat. No. 5,281,408, which is a division of Ser. No. 680,984, Apr. 5, 1991, Pat. No. 5,205,290.

[51] Int. Cl.$^6$ ............. A61K 49/04; A61K 9/14; A61B 6/00
[52] U.S. Cl. ............ 424/9.4; 424/9.51; 424/9.52; 424/450; 424/489; 128/654
[58] Field of Search ............... 424/9.4, 9.411, 424/9.42, 9.43, 9.52, 9.51, 9.5, 450, 489, 9.321, 497, 501; 128/662.02, 654

[56] References Cited

U.S. PATENT DOCUMENTS

| | | | |
|---|---|---|---|
| 3,015,128 | 1/1962 | Sommerville et al. | 18/2.6 |
| 3,293,114 | 12/1966 | Kenage et al. | 162/168 |
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,594,326 | 7/1971 | Himmel et al. | 252/316 |
| 3,615,972 | 10/1971 | Morehouse et al. | 156/79 |
| 3,732,172 | 5/1973 | Herbig et al. | 252/316 |
| 3,873,564 | 3/1975 | Schneider et al. | 260/309.6 |
| 3,945,956 | 3/1976 | Garner | 260/2.5 B |
| 3,960,583 | 6/1976 | Netting et al. | 106/122 |
| 4,089,801 | 5/1978 | Schneider | 252/316 |
| 4,108,806 | 8/1978 | Cohrs et al. | 521/54 |
| 4,138,383 | 2/1979 | Rembaum et al. | 260/29.7 H |
| 4,162,282 | 7/1979 | Fulwyler et al. | 264/9 |
| 4,179,546 | 12/1979 | Garner et al. | 521/56 |
| 4,192,859 | 3/1980 | Mackaness et | 424/5 |
| 4,224,179 | 9/1980 | Schneider | 252/316 |
| 4,229,360 | 10/1980 | Schneider et al. | 260/403 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,657 | 5/1982 | Morris | 424/38 |
| 4,344,929 | 8/1982 | Bonsen et al. | 424/15 |
| 4,420,442 | 12/1983 | Sands | 264/13 |
| 4,421,562 | 12/1983 | Sands et al. | 106/75 |
| 4,426,330 | 1/1984 | Sears | 206/403 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon | 424/1.1 |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |

(List continued on next page.)

FOREIGN PATENT DOCUMENTS

| | | |
|---|---|---|
| B-30351/89 | 3/1993 | Australia . |
| 0 107 559 | 5/1984 | European Pat. Off. . |
| 0077752 B1 | 3/1986 | European Pat. Off. . |
| 0 231 091 | 8/1987 | European Pat. Off. . |
| 0243947 | 11/1987 | European Pat. Off. . |
| 0 272 091 | 6/1988 | European Pat. Off. . |
| 0320433 | 12/1988 | European Pat. Off. . |
| 0 324 938 | 7/1989 | European Pat. Off. . |
| 0 338 971 | 10/1989 | European Pat. Off. . |
| 0 361 894 | 4/1990 | European Pat. Off. . |
| 0 216 730 | 1/1991 | European Pat. Off. . |
| 0357164 | 10/1991 | European Pat. Off. . |
| 0 458 745 A1 | 11/1991 | European Pat. Off. . |
| 0467031 | 1/1992 | European Pat. Off. . |

(List continued on next page.)

OTHER PUBLICATIONS

PR Newswire, Apr. 1, 1986.
Swanson et al., Chapter 22, "Enhancement Agents for Ultrasound: Fundamentals", *Pharmaceuticals In Medical Imaging*, pp. 682–687 (1990).
Ophir et al., "Contrast Agents in Diagnostic Ultrasound", *Ultrasound in Med. & Biol.*, vol. 15, No. 4, pp. 319–333 (1989).
Jacobs, "Intraocular gas measurement using A–scan ultrasound", *Current Eye Research*, vol. 5, No. 8, pp. 575–578 (1986).
Chang et al., "Semipermeable Aqueous Microcapsules", *Canadian J. Of Phys. And Pharm.*, 1996, 44, 115–128.
Chang, "Semipermeable Microcapsules", *Science*, 1964, 146, 524–525.

(List continued on next page.)

*Primary Examiner*—Gary E. Hollinden
*Assistant Examiner*—Michael G. Hartley
*Attorney, Agent, or Firm*—Woodcock Washburn Kurtz Mackiewicz & Norris LLP

[57] ABSTRACT

Novel gas filled microspheres useful as computed tomography (CT) contrast agents. The microspheres are prepared from a gas and/or a gaseous precursor, and one or more stabilizing compounds.

51 Claims, 3 Drawing Sheets

U.S. PATENT DOCUMENTS

| | | | |
|---|---|---|---|
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et | 424/426 |
| 4,900,540 | 2/1990 | Ryan et al. | 424/9 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,008,050 | 4/1991 | Cullis et al. | 264/4.3 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,114,703 | 5/1992 | Wolf et al. | 424/5 |
| 5,123,414 | 6/1992 | Unger | 128/654 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,358,702 | 10/1994 | Unger | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,393,530 | 2/1995 | Schneider et al. | 424/450 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |
| 5,487,390 | 1/1996 | Cohen et al. | 128/662.02 |
| 5,496,535 | 3/1996 | Kirkland | 424/9.37 |
| 5,496,536 | 3/1996 | Wolf | 424/9.322 |
| 5,498,421 | 3/1996 | Grinstaff et al. | 424/450 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,547,656 | 8/1996 | Unger | 424/9.4 |
| 5,552,133 | 9/1996 | Lambert et al. | 424/9.52 |
| 5,556,610 | 9/1996 | Yan et al. | 424/9.52 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,560,364 | 10/1996 | Porter | 128/662.02 |
| 5,562,893 | 10/1996 | Lohrmann | 424/9.52 |
| 5,567,413 | 10/1996 | Klaveness et al. | 424/9.51 |
| 5,567,414 | 10/1996 | Schnider et al. | 424/9.52 |
| 5,567,765 | 10/1996 | Moore et al. | 524/801 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,595,723 | 1/1997 | Quay | 424/9.5 |
| 5,606,973 | 3/1997 | Lambert et al. | 128/662.02 |
| 5,620,689 | 4/1997 | Allen et al. | 424/178.1 |
| 5,643,553 | 7/1997 | Schneider et al. | 424/9.52 |
| B1 4,229,360 | 11/1991 | Schneider et al. | 260/403 |

FOREIGN PATENT DOCUMENTS

| | | |
|---|---|---|
| 0 314 764 B1 | 3/1992 | European Pat. Off. . |
| 0 554 213 A1 | 8/1993 | European Pat. Off. . |
| 0 727 255 A2 | 8/1996 | European Pat. Off. . |
| 62-286534 SHO | 12/1987 | Japan . |
| 63-60943 | 3/1988 | Japan . |
| 1044680 | 10/1966 | United Kingdom . |
| 2193095 | 2/1988 | United Kingdom . |
| WO 80/02365 | 11/1980 | WIPO . |
| WO 82/01642 | 5/1982 | WIPO . |
| US85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| 0357163 | 3/1990 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| 0441468 | 8/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/17212 | 10/1992 | WIPO . |
| WO 92/17213 | 10/1992 | WIPO . |
| WO 92/17436 | 10/1992 | WIPO . |

| | | |
|---|---|---|
| WO 92/21382 | 12/1992 | WIPO . |
| WO 93/00933 | 1/1993 | WIPO . |
| WO 93/05819 | 1/1993 | WIPO . |
| WO 93/06869 | 4/1993 | WIPO . |
| WO 92/13809 | 7/1993 | WIPO . |
| WO 93/17718 | 9/1993 | WIPO . |
| WO 93/20802 | 10/1993 | WIPO . |
| WO 94/06477 | 3/1994 | WIPO . |
| WO 94/09829 | 5/1994 | WIPO . |
| WO 94/16739 | 8/1994 | WIPO . |
| WO 94/21302 | 9/1994 | WIPO . |
| WO 94/28780 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 96/04018 | 2/1996 | WIPO . |
| WO 96/09793 | 4/1996 | WIPO . |
| WO 96/36286 | 11/1996 | WIPO . |

OTHER PUBLICATIONS

Deasy, *Microencapsulation and Related Drug Processes*, 1983, vol. 20, Chs. 9 and 10, 195–240 (Marcel Dekker, Inc. NY).

Yeung et al., "Preparation of Microencapsulated Liposomes", *J. Microencapsulation*, 1988, 5, 331–337.

Mattrey et al., *Gas Emulsions as Ultrasound Contrast Agents; Preliminary Results in Rabbits and Dogs*, *Investigative Radiology*, vol. 29, Jun. Supp. 2, pp. S139–S141, 1994.

Meltzer et al., *Transmission of Ultrasonic Contrast Through the Lungs*, *Ultrasound in Med. & Biol.*, vol. 7, No. 4, 377–384, 1981.

Miller, Ultrasonics (Sep. 1981), "Ultrasonic detection of resonant cavitation bubbles in a flow tube by their second–harmonic emissions," pp. 217–224.

Dittrich, "Cardiac Muscle Ischemia and Infarction", The Second Annual International Symposium on Contrast Agents in Diagnostic Ultrasound, Atlantic City, NJ (May 7, 1996) (abstract).

Pantely, "Intravenous Contrast Echocardiography–Tissue Imaging & Quantification of Coronary Blood Flow", The Second Annual International Symposium on Contrast Agents in Diagnostic Ultrasound, Atlantic City, NJ (May 7, 1996) (abstract).

Schutt et al., "Osmotically Stabilized Microbubble Sonographic Contrast Agents", Acad. Radiol., vol. 3, Suppl. 2, pp. S188–S190 (Aug. 1996).

Frézard, et al., "Permeability and stabiltiy in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/ Sustaining of Drugs and Stability in Human Serum", *Art, Cells, Blood Subs., and Immob. Biotech.*, 22(4), pp. 1403–1408 (1994).

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypridoxal", *Biochemistry*, vol. 9, No. 3, pp. 525–532 (1970).

Stelmashok et al., *Koordinatsionnaya Khimiya* vol. 3, No. 4, pp. 524–527 (1997) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., Metal Ions in Biological Systems: Antibiotics and Their Complexes, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multiamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agents: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp.167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp.77–80 (1989).

Mann et al., "Formation of Iron Oxides in Unilamellar Vesicles", *Journal of Colloid and Interface Science*, vol. 122, No.2, pp. 326–335 (1988).

Anderson et al., "Manganese (III) Complexes in Oxidative Decarboxylation of Acids", *J. Am. Chem. Soc.*, vol. 92, No.8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Pariculate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E. "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250 (3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics* vol. 220, pp. 477–484 (1983).

Dorland's Illustrated Medical Dictionary, p. 946, 27th ed. (W.B. Saunders Company, Philadelphia 1988).

Liposome Technology, Gregoriadis, G., ed., vol. I, pp. 1–18, 29–35, 51–65 and 79–107 (CRC Press Inc., Boca Raton, FL, (1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiaby Low–frequency Synthesized Ultrasound", *IEEE Engineering*, pp. 879–880, vol. 2 (abstract), (1987).

McAvoy et al., *IEEE Engineering*, Ultrasonics Symposium Proceedings, vol. 2, pp. 677–1248 (abstract), (1989).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Prepartion of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol. 3*, 1978, 341–350.

Chiellini et al., *Polymers in Medicine II: Biomedical and Pharmaceutical Applications*, (Plenum Press, New York and London) pp. 387–396, (1983).

deGier et al., "Relations Between Liposomes and Biomembranes", *Annals of The New York Academy of Sciences*, 1978, 308:85–99.

Felgner et al., "Lipofection: A highly efficient lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

*Mammalian Cells Biotechnology*: A Practical Approach, M. Butler, 1991 (Oxford University Press, New York), pp. 57–70.

Mathiowitz et al., "Photochemical Rupture of Microcapsules: A Model System", *Journal of Applied Polymer Science*, 1981, 26:809–822.

May et al., "Cationic Liposomes Enable Bovine Herpesvirus Type 2 DNA to Infect Cells", *Acta virol.*, 1991, 35:107.

Poznansky et al., "Biologica Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res. 1992* , 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phases", *Science 1992*, 258:744–746.

Trubetskoy et al. "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbology] 1992, 58:67–69.

Woodle et al., "Versatiltiy in lipid compositions showing prolonged circulation . . . ", *Biochimica et Biophysica Acta 1992*, 1105:193–200.

Zhou et al., "Targeted delivery of DNA by liposomes and polymers", *J. of Controlled Release 1992*, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific, 1991), "Syringes", pp. 1511–1513; Filtration, Syringe Filters, pp. 766–768; Filtration Membranes, pp. 750–753; Filtration, Filter Holders, p. 744, (1991).

Gramiak et al., *Radiology*, "Detection of Intracardiac Blood Flow by Pulsed Echo–Ranging", pp. 415–418 (1971).

Feigenbaum et al., *Circulation*, "Identification of Ultrasound Echoes from the Left Ventricle by Use of Intracardiac Injections of Indocyanine Green", vol. XLl, pp. 615–621 (1970).

Santaella, et al., *FEBS 13463*, "Extended In Vivo Blood Circulation Time of Fluorinated Liposomes", vol. 336, No. 3, pp. 481–484 (1993).

Kost, et al, *Polymers in Medicine II*, Ultrasonic Modulated Drug Delivery Systems, pp. 387–396, (1988).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian, *Physical Pronciples and Instrumentation*, "Computed Body Tomography", Chapter 1, pp. 1–7, (1985).

Aronberg, *Techniques*, "Computed Body Tomography", Chapter 2, pp. 9–36, (1985).

*Matheson Gas Data Book*, Matheson Company, Inc. 1966.

METHODS OF COMPUTED TOMOGRAPHY USING PERFLUOROCARBON GASEOUS FILLED MICROSPHERES AS CONTRAST AGENTS

CROSS-REFERENCE TO RELATED APPLICATIONS

This is a continuation-in-part of U.S. application Ser. No. 08/247,656, filed May 23, 1994, now abandoned, and a continuation-in-part of U.S. application Ser. No. 08/116,982, filed Sep. 7, 1993, now U.S. Pat. No. 5,456,900, issued Oct. 10, 1995, which is a division of U.S. application Ser. No. 07/980,594, filed Jan. 19, 1993, now U.S. Pat. No. 5,281,408, issued Jan. 25, 1994, which is a division of U.S. application Ser. No. 07/680,984, filed Apr. 5, 1991, now U.S. Pat. No. 5,205,290, issued Apr. 27, 1993.

The disclosures of each of the above applications are incorporated herein by reference in their entirety.

FIELD OF THE INVENTION

The present invention relates to compositions for computed tomography. More particularly, the present invention relates to compositions for computed tomography which comprise gas-filled microspheres.

BACKGROUND OF THE INVENTION

Computed tomography (CT) is a diagnostic imaging technique which measures, in its imaging process, the radiodensity of matter. Radiodensity of matter is typically expressed in Hounsefield Units (HU). Hounsefield Units are a measure of the relative absorption of computed tomography X-rays by matter and is directly proportional to electron density. Water has arbitrarily been assigned a value of 0 HU, air a value of −1000 HU, and dense cortical bone a value of 1000 HU.

Various tissues in the body possess similar densities. Difficulty has been encountered in generating by CT visual images of tissues which possess similar densities and which are proximate each other. For example, it is difficult to generate separate CT images of the gastrointestinal (GI) tract and adjacent structures, including, for example, the blood vessels and the lymph nodes. Accordingly, contrast agents have been developed in an attempt to change the relative density of different tissues, and thereby improve the diagnostic efficacy of CT.

A commonly used contrast agent for computed tomography, particularly in connection with scans of the GI tract for increasing the radiodensity of the bowel lumen, is barium sulfate. Barium sulfate increases electron density in certain regions of the body, and is classified as a "positive contrast agents."

Currently available CT contrast agents, including barium compounds, such as barium sulfate, suffer from various drawbacks. For example, the viability of CT agents is generally extremely sensitive to concentration. If the concentration is too low, little contrast is observed. If the concentration is too high, beam hardening artifacts result and are observed as streaks in the CT images. In addition, difficulty is generally encountered in visualizing the bowel mucosa with the currently available contrast agents.

Lipid compositions, for example, lipid emulsions and/or suspensions, have been formulated as contrast agents, particularly for the GI tract. Lipids inherently possess an electron density that is lower than water. Accordingly, lipid compositions are capable of decreasing electron density and are generally termed "negative contrast agents".

Lipid compositions are capable of providing enhanced visualization in CT scans. However, lipid-based contrast agents also suffer from various drawbacks. For example, compositions which comprise lipid alone are generally unpalatable which limits their use for oral applications. In addition, lipid compositions are typically expensive to formulate. Undesirable side effects can also be caused from the high concentrations of lipid which are frequently used in the lipid-based contrast agents to achieve adequate negative contrast in certain regions of the body, for example, the bowel lumen. Patients with pancreatitis, peptic or gastric ulcers, irritable bowel disease, Crohn's disease, or colitis are especially prone to such side effects. Furthermore, lipid-based contrast agents are typically perishable and thus possess a limited shelf-life.

Accordingly, new and/or better contrast agents for CT are needed. The present invention is directed to this, as well as other, important ends.

BRIEF DESCRIPTION OF THE PRIOR ART

In U.S. Pat. No. 5,205,290 referred to above, there is disclosed low density microspheres serving as contrast agents for computed tomography, which are composed of biocompatible synthetic polymers or copolymers prepared from monomers, such as acrylic acid, methacrylic acid, ethyleneimine, acrylamide, ethylene glycol, N-vinyl-2-pyrrolidone, and the like. In a preferred synthesis protocol, the microspheres are prepared using a heat expansion process in which the microspheres, made from an expandable polymer or copolymer, contain in their void or cavity, a volatile liquid. The microspheres are then heated, plasticizing the microspheres and volatilizing the liquid, causing the microspheres to expand to up to about several times their original size. When the heat is removed, the thermoplastic polymer retains at least some of its expanded shape. Microspheres produced by this process tend to be of particularly low density, and are thus said to be preferred.

Volatile liquids useful in the heat expansion process of U.S. Pat. No. 5,205,290 include aliphatic hydrocarbons, such as ethane; chlorofluorocarbons, such as $CCl_3F$; tetraalkyl silanes, such as tetramethyl silane; as well as perfluorocarbons, such as those having between 1 and about 9 carbon atoms and between about 4 and about 20 fluorine atoms, especially $C_4F_{10}$. It is said to be important that the volatile liquid not be a solvent for the microsphere polymer or copolymer; and that the volatile liquid should have a boiling point that is below the softening point of the microsphere polymer or copolymer.

The stabilized gaseous precursor filled microspheres used as contrast media in the present invention are distinguishable from those of U.S. Pat. No. 5,205,290 in that they are not made from a polymer or copolymer by a heat expansion process, and are not, therefore, subject to the same limitations which require that the volatile liquid not be a solvent for, and not have a boiling point below the softening point of, the microsphere polymer or copolymer.

D'Arrigo, U.S. Pat. Nos. 4,684,479 and 5,215,680 disclose gas-in-liquid emulsions and lipid-coated microbubbles, respectively, which are stable and said to be useful in several fields, including as contrast agents for echocardiography, and in the ultrasonic monitoring of local blood flow. However, there is no suggestion that these compositions would be useful as contrast media for computed tomography.

Quay published application WO 93/05819 discloses that gases with high Q numbers are ideal for forming stable gases, and that "microbubbles" of these gases are useful as contrast agents in ultrasound imaging. However, the disclosure is limited to stable gases, rather than their stabilization and encapsulation, as in the present invention; although in a preferred embodiment described on page 31, sorbitol is used to increase viscosity, which in turn is said to extend the life of a microbubble in solution. Also, it is not an essential requirement of the present invention that the gas involved have a certain Q number or diffusibility factor. Quay contains no suggestion that the gas microbubbles would be effective as a contrast medium for computed tomography.

Vanderipe published application WO 93/06869 also discloses the use of bubbles of gases and gas mixtures, including perfluorocarbons, as ultrasound imaging enhancement agents. Again, however, these gas bubbles are not encapsulated and there is no suggestion of their use as contrast media for computed tomography.

Lanza et al., published application WO 93/20802 discloses acoustically reflective oligolamellar liposomes for ultrasonic image enhancement, which are multilamellar liposomes with increased aqueous space between bilayers or have liposomes nested within bilayers in a nonconcentric fashion, and thus contain internally separated bilayers. Their use in monitoring a drug delivered in a liposome administered to a patient, is also described. However, there is no suggestion that these liposomes could serve as contrast media for computed tomography.

Widder et al., published application EP-A-0 324 938 discloses stabilized microbubble-type ultrasonic imaging agents produced from heat-denaturable biocompatible proteins, e.g., albumin, hemoglobin, and collagen. Again, however, use of such compositions as contrast media for computed tomography is not described.

There is also mentioned a presentation believed to have been made by Moseley et al. at a 1991 Napa, Calif. meeting of the Society for Magnetic Resonance in Medicine, which is summarized in an abstract entitled "Microbubbles: A Novel MR Susceptibility Contrast Agent". The microbubbles which are utilized comprise air coated with a shell of human albumin. The stabilized gas-filled microspheres of the present invention are not suggested, nor is their use as contrast media for computed tomography.

Tei et al., unexamined patent application disclosure SHO 63-60943 discloses contrast agents for ultrasonic diagnosis comprising a perfluorocarbon emulsion with an emulsion particle size of 1 to 10 μm, in which the perfluorocarbon is preferably 9 to 11 carbon atoms and the emulsifier may be, for example, a phospholipid or a nonionic polymeric surfactant such as poly(oxyethylene)-poly(oxypropylene) copolymers. The emulsion may be prepared by utilizing a mixer. There is no suggestion, however, that these perfluorocarbon emulsions would be suitable for use as contrast media in computed tomography.

Knight et al., U.S. Pat. 5,049,388 discloses small particle aerosol liposome and liposome-drug combinations for medical use, for example, as systems for delivering drugs to the respiratory tract by inhalation. However, there is no suggestion that these liposomes can be gaseous precursor filled or that they might serve as contrast media for computed tomography.

SUMMARY OF THE INVENTION

The present invention is directed to a contrast medium useful for computed tomography imaging, said contrast medium comprising stabilized gas and gaseous precursor filled microspheres, wherein the gas may be, for example, air or nitrogen, but may also be derived from a gaseous precursor, for example, perfluoropentane, and the microspheres are stabilized by being formed from a stabilizing compound, for example, a biocompatible lipid or polymer. In certain preferred embodiments, the biocompatible lipid comprises a phospholipid which is in the form of a lipid bilayer. A contrast medium in accordance with the present invention comprises a substantially homogenous as well as surprisingly stable suspension of microspheres comprising gas and stabilizing compound. A unique aspect of the present invention involves the use of perfluorocarbon gases which are capable of maintaining the integrity, and thus, enhancing the stability, of the microspheres.

The present invention also concerns a method for preparing stabilized gas-filled microspheres for use as computed tomography imaging contrast media, comprising the step of agitating an aqueous suspension of a stabilizing compound, for example, a biocompatible lipid or polymer, so that stabilized gas-filled microspheres result. Desirably, this step is carried out at a temperature below the gel to liquid crystalline phase transition temperature of the biocompatible lipid so as to achieve a stabilized gas-filled microsphere product.

The present invention further pertains to a method of providing an enhanced image of an internal region of a patient comprising (i) administering to the patient one or more of the present contrast media, and (ii) scanning the patient using computed tomography imaging to obtain visible images of the involved regions.

Also encompassed by the present invention is a method for diagnosing the presence of diseased tissue in a patient, especially in the gastrointestinal regions of the patient, comprising (i) administering to the patient one or more of the present contrast media, and (ii) scanning the patient using computed tomography imaging to obtain visible images of any diseased tissue in the region.

The present invention further relates to a method for preparing in situ in the tissue of a patient a contrast medium for computed tomography, the contrast medium comprising gas-filled microspheres, comprising (i) administering to the patient gaseous precursor-filled microspheres, and (ii) allowing the gaseous precursor to undergo a phase transition from a liquid to a gas to provide the gas-filled microspheres.

All of the above aspects of the present invention can be carried out, often with considerable attendant advantage, especially with regard to ease of ingestion by a patient, by using gaseous precursors to form the gas of the gas-filled microspheres. Once ingested, and upon gas formation in, for example, the gastrointestinal tract, expansion of the gaseous precursor causes an increase in the volume of the contrast medium and impart low density to the gastrointestinal tract, thereby enhancing computed tomography imaging thereof. These gaseous precursors may be activated by a number of factors, but preferably are temperature activated, that is, they are activated by exposure to elevated temperature. Such gaseous precursors are compounds which, at a selected activation or transition temperature, change phases from a liquid to a gas. Activation thus takes place by increasing the temperature of the compound from a point below, to a point above, the activation or transition temperature. Optionally, the contrast medium may further comprise a liquid fluorocarbon compound, for example, a perfluorocarbon, to further stabilize the microspheres. Preferably, the fluorocarbon liquid is encapsulated by the microspheres.

The present invention also relates to a method for preparing stabilized gas or gaseous precursor filled microspheres for use as a computed tomography imaging contrast medium. The method comprises agitating an aqueous suspension of a lipid (that is, the lipid stabilizing compound), in the presence of a gas or gaseous precursor, resulting in gas or gaseous precursor filed microspheres. Desirably, agitation is carried out at a temperature below the gel to liquid crystalline phase transition temperature of the lipid to achieve a preferred product.

Where a gaseous precursor is used, the gaseous precursor filled microsphere composition is generally maintained at a temperature at which the gaseous precursor is liquid until administration to the patient. At the time of administration the temperature may, if desired, be raised to activate the gaseous precursor to form a gas. The resulting gas filled microspheres are then administered to the patient. Alternatively, the gaseous precursor filled microspheres may, if desired, be administered without raising the temperature, and the gaseous precursor allowed to form a gas as a result of the naturally elevated internal temperature of a patient. The composition may be agitated, if necessary, prior to administration.

The present invention further pertains to a method of providing an enhanced image of an internal region of a patient, especially an image of the gastrointestinal region of said patient, said method comprising (i) administering to the patient the foregoing contrast medium, and (ii) scanning the patient using computed tomography imaging to obtain visible images of said region.

The present invention also encompasses a method for diagnosing the presence of diseased tissue in a patient, especially in the gastrointestinal regions of said patient, said method comprising (i) administering to the patient the foregoing contrast medium, and (ii) scanning the patient using computed tomography imaging to obtain visible images of any diseased tissue in the region.

These and other aspects of the invention will become more apparent from the following detailed description when taken in conjunction with the following drawings.

BRIEF DESCRIPTION OF THE DRAWINGS

It should be noted that, for purposes of making the drawings more readily understood, only single bilayers are shown. In fact, the membranes which these drawings illustrate may be either monolayers, bilayers, oligolamellar, or multilamellar. Consequently, the figures described below should in no way be taken as limiting the present invention to microspheres whose envelope or skin is comprised of only a single layer or bilayer of stabilizing compound.

DETAILED DESCRIPTION OF THE INVENTION

Figure 1:
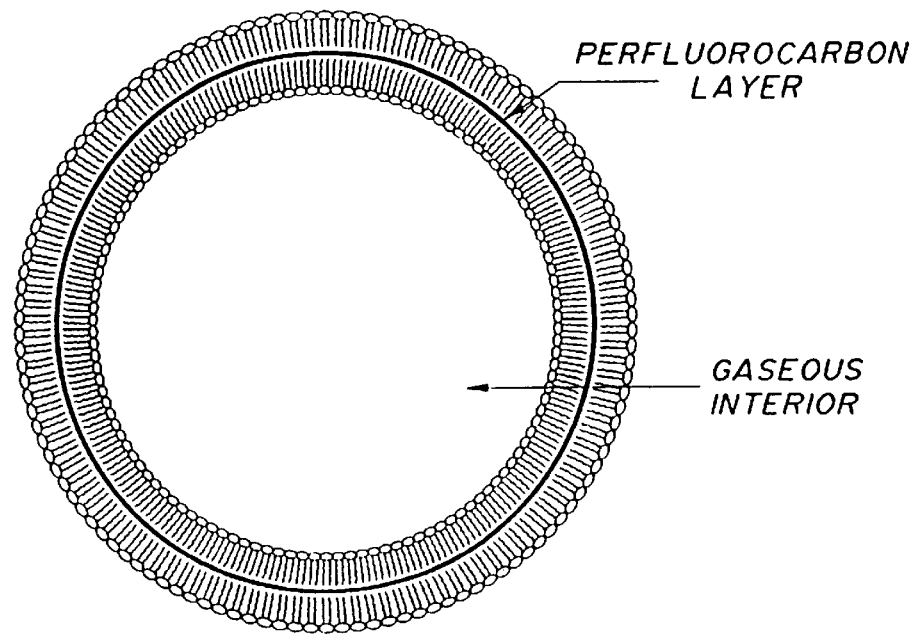
FIG. 1 depicts the stabilization of a gas-filled lipid bilayer microsphere with a perfluorocarbon that is proximate the hydrophobic tails of the lipids.
Figure 2:
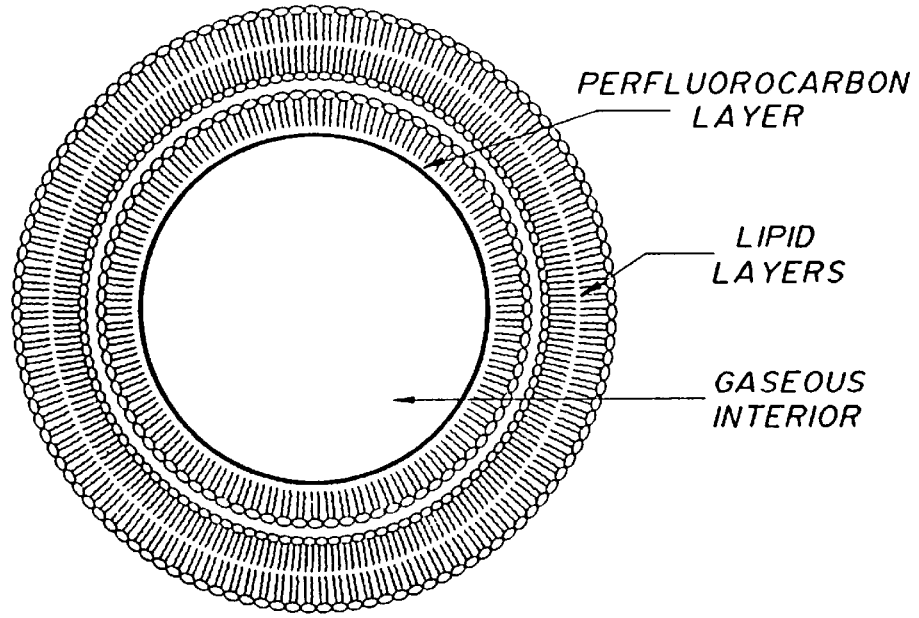
FIG. 2 depicts the stabilization of a gas-filled lipid oligolamellar microsphere with a perfluorocarbon that is proximate the hydrophobic tails of lipids in a monolayer that is located within a lipid bilayer.
Figure 3:
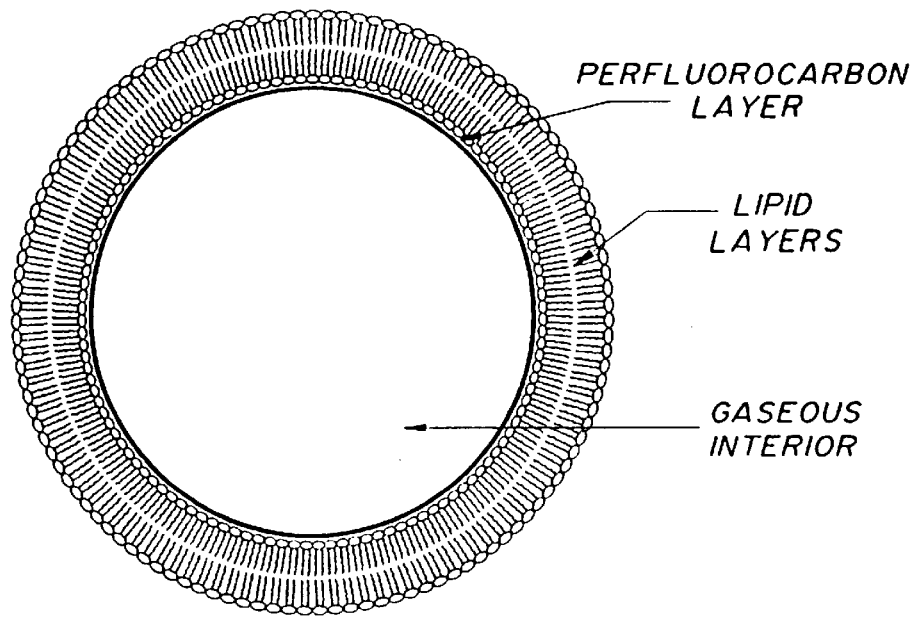
FIG. 3 depicts the stabilization of a gas-filled lipid bilayer microsphere with a perfluorocarbon that is proximate the interior hydrophilic head groups of the lipids.
Figure 4:
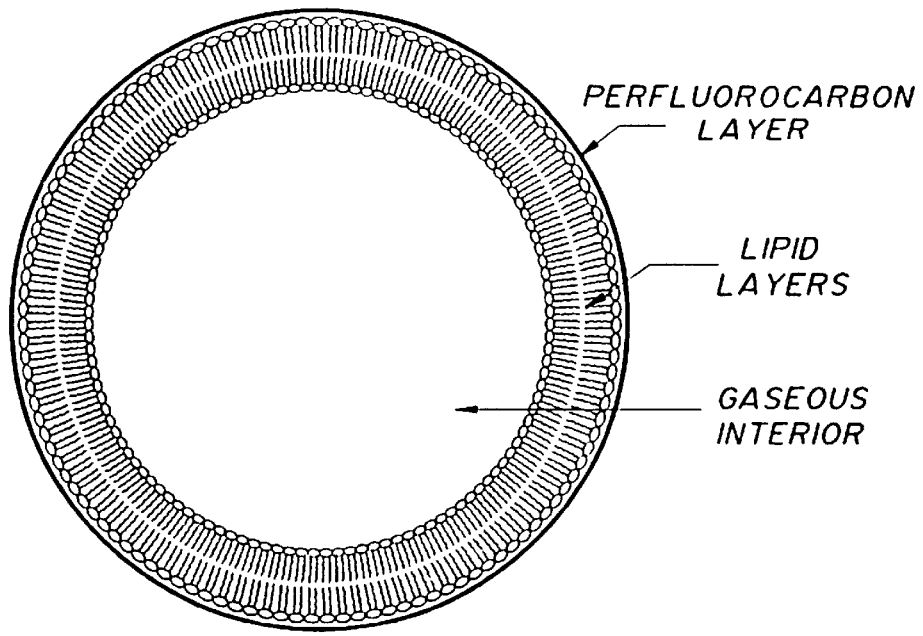
FIG. 4 depicts the stabilization of a gas-filled lipid bilayer microsphere with a perfluorocarbon that is proximate the exterior hydrophilic head groups of the lipids.
Figure 5:
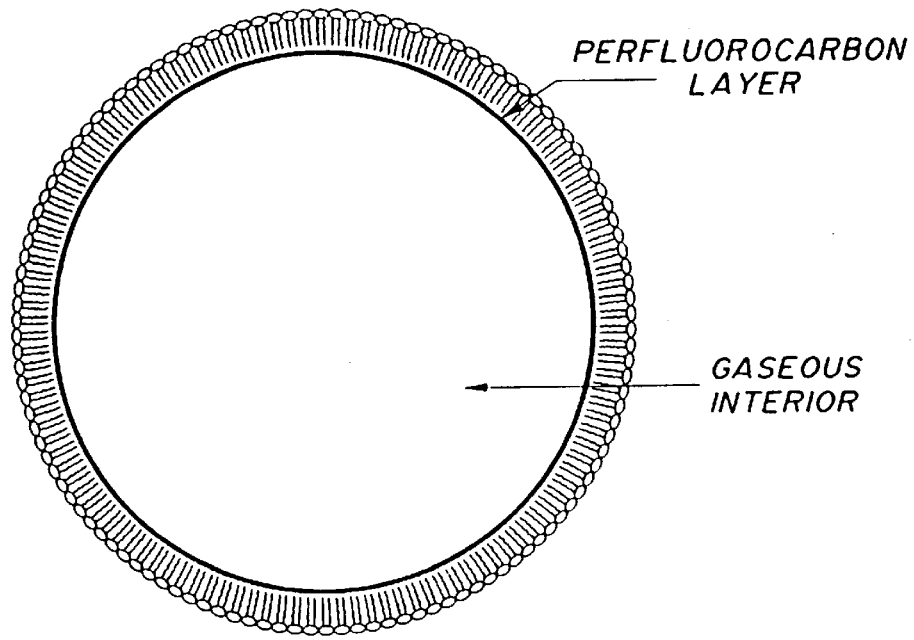
FIG. 5 depicts the stabilization of a gas-filled lipid monolayer microsphere with a perfluorocarbon that is proximate the interior hydrophobic tails of the lipids.
Figure 6:
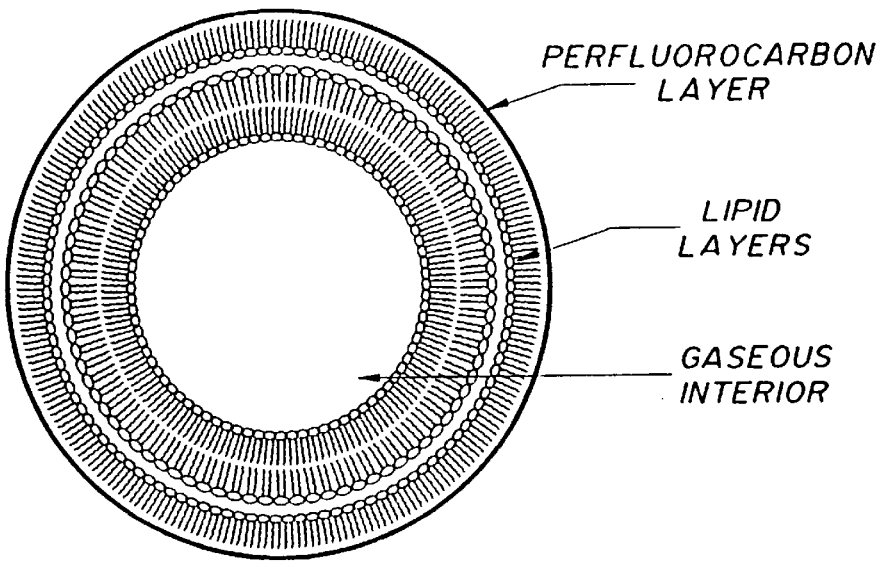
FIG. 6 depicts the stabilization of a gas-filled lipid oligolamellar microsphere with a perfluorocarbon that is proximate the hydrophobic tails of lipids in a monolayer that is located outside of a lipid bilayer.

As employed above and throughout the disclosure, the following terms, unless otherwise indicated, shall be understood to have the following meanings.

"Stabilized" refers to microspheres which are substantially resistant to degradation that is caused, for example, by the loss of structural or compositional integrity in the walls of the microspheres and/or by the loss of any significant portion of the gas or gaseous precursor which is encapsulated within the microsphere.

"Lipid" refers to a synthetic, semisynthetic or naturally-occurring amphipathic compound which comprises a hydrophilic component and a hydrophobic component. Lipids include, for example, fatty acids, neutral fats, phosphatides, glycolipids, aliphatic alcohols and waxes, terpenes and steroids.

"Microsphere" refers to a small spherical entity which is characterized by the presence of an internal void. Preferred microspheres are formulated from lipids, including the various lipids described herein. In any given microsphere, the lipids may be in the form of a monolayer or bilayer, and the mono- or bilayer lipids may be used to form one or more mono- or bilayers. In the case of more than one mono- or bilayer, the mono- or bilayers are generally concentric. The lipid microspheres described herein include such entities commonly referred to as liposomes, micelles, bubbles, microbubbles, and the like. Thus, the lipids may be used to form a unilamellar microsphere (comprised of one monolayer or bilayer), an oligolamellar microsphere (comprised of about two or about three monolayers or bilayers) or a multilamellar microsphere (comprised of more than about three monolayers or bilayers). The internal void of the microspheres may be filled with a liquid, including, for example, an aqueous liquid, a gas, a gaseous precursor, and/or a solid or solute material, as desired.

"Liposome" refers to a generally spherical cluster or aggregate of amphipathic compounds, including lipid compounds, typically in the form of one or more concentric layers, for example, bilayers. They may also be referred to herein as lipid microspheres.

"Polymer" refers to molecules formed from the chemical union of two or more repeating units. Accordingly, included within the term "polymer" are, for example, dimers, trimers and oligomers. In preferred form, the term "polymer" refers to molecules which comprise 10 or more repeating units.

"Semi-synthetic polymer" refers to a naturally-occurring polymer that has been chemically modified. Exemplary naturally-occurring polymers include, for example, polysaccharides.

"Patient" refers to animals, including mammals, preferably humans.

The present invention is directed, inter alia, to contrast media comprising stabilized gas filled microspheres which are basically bubbles of very small diameter comprising a "skin" or "envelope" of a stabilizing compound that surrounds or encloses a cavity or void filled with liquid or gas. The stabilizing compound provides integrity to the microsphere such that the microspheres exist for a useful period of time. The stabilized microspheres are particularly suitable for use as contrast agents for computed tomography (CT). In embodiments where the stabilizing compound comprises, for example, a lipid, the microspheres possess a lower electron density relative to water. This lower electron density imparts highly desirable properties to the contrast agents of the present invention, particularly with respect to CT imaging.

The stabilized microspheres of the present invention comprise a gas and/or a gaseous precursor. Any of the various biocompatible gas and gaseous precursors may be used in the gas and gaseous precursor filled microspheres of the present invention. Preferred gases are gases which are inert and which are biocompatible, that is, gases which are not injurious to biological function. Preferred gases also have a low solubility and diffusibility in aqueous media.

Moreover, it is possible to utilize a gas and a gaseous precursor together. A unique and preferred aspect of the present invention results from the discovery that when a gaseous precursor, for example, a perfluorocarbon, is combined with a gas ordinarily used to make the stabilized microspheres of the present invention, microspheres are obtained having an added degree of stability not otherwise obtainable with the gas alone. Thus, it is a preferred aspect of the invention to utilized gaseous precursors which can be activated, for example, upon exposure to elevated temperatures, to form stabilized microspheres in the form, for example, of stable foams, which can be utilized as effective low density contrast agents for computed tomography.

Stabilized microspheres made with gaseous precursors have several advantages. First, as the gases generated from gaseous precursors tend to be insoluble and relatively non-diffusible, these gases can be stabilized for use as contrast media for computed tomography. Because the gases are relatively stable, less stabilizing compound is necessary than would be required for more soluble and diffusible gases, such as nitrogen or air. In general, a thicker walled skin or envelope of stabilizing compound, for example, a thick walled microsphere, is necessary to stabilize gases such as air or nitrogen. While thick walled microspheres filled with air, nitrogen or other gases can be used as CT contrast agents, the thick walls of such microspheres raise the effective density of the contrast medium, which may in turn limit the effectiveness of the contrast medium. Furthermore, thick walled microspheres may be relatively unpalatable for oral ingestion, or may be difficult to metabolize following intravenous injection. With the gaseous precursors used in the present invention, for example, a perfluorocarbon, the stabilizing compounds can be less rigid and the resulting microspheres can be thinner walled and easier to metabolize, yet still possess sufficient stabilizing compound to stabilize the microsphere.

As is described in more detail further below, the stabilized microspheres used in the present invention may be formed simply by agitation of the stabilizing compound in an aqueous environment and in the presence of a gas and/or gaseous precursor. Where a gaseous precursor is used, the gaseous precursor filled microsphere contrast medium which has been prepared, before administration to a patient, is desirably maintained at a temperature at which the gaseous precursor is liquid. At the time of administration, it can be pre-shaken and then ingested as a preformed foam. Alternatively, the contrast medium can be ingested as a suspension to form a foam in situ within, for example, the stomach and gastrointestinal tract of a patient. The bowel motility serves to mix the gaseous precursor within the stabilizing compound and the increase in temperature serves to form the gas filled microsphere based foam in situ within the bowel. A preferred embodiment described in detail further below involves incorporating a suitable viscosity modifying agent, for example, a natural and semi-natural gum, cellulose or synthetic polymer, for example, polyethyleneglycol. In the presence of such a viscosity modifying agent and the stabilizing compound, the gas bubbles as they are generated are coated with these compounds and become stabilized through this coating process, whereby the contrast medium of the present invention is formed.

Thus, the microspheres are formed from, or created out of, a matrix of stabilizing compounds which permit the gas filled microspheres to be established and thereafter retain their size and shape for the period of time required to be useful in computed tomography imaging. These stabilizing compounds include those which have a hydrophobic/hydrophilic character which allows them to form bilayers, and thus microspheres, in the presence of water. Thus, water, saline or some other water-based medium, often referred to hereafter as a diluent, is an important aspect of the stabilized gas and gaseous precursor filled microsphere contrast agents of the present invention, particularly in embodiments involving microspheres which comprise bilayers.

The stabilizing compound may be a mixture of compounds which contribute various desirable attributes to the stabilized microspheres. For example, compounds which assist in the dissolution or dispersion of the fundamental stabilizing compound have been found advantageous. The gas, which can be a gas at the time the microspheres are made, or can be a gaseous precursor which, in response to an activator, such as elevated temperature, is transformed from the liquid phase to the gas phase. The various aspects of the stabilized gas and gaseous precursor filled contrast agents of the present invention will now be described, starting with the gases and gaseous precursors.

Gases and Gaseous Precursors

The microspheres of the present invention are essentially stabilized bubbles which encapsulate a gas and/or a gaseous precursor. The gases and/or precursors thereto provide the compositions with increased negative density. This increases their effectiveness as contrast agents for CT.

Preferred gases are gases which are extremely stable. The term stable gas, as used herein, refers to gases which are substantially inert and which are biocompatible, that is, gases which are not injurious to biological functions and which will not result in any degree of unacceptable toxicity, including allergenic responses and disease states. Preferred also are gases which have low solubility and/or diffusibility in aqueous media. Gases, such as perfluorocarbons, are less diffusible and are relatively insoluble in aqueous media. Accordingly, they are easier to stabilize into the form of bubbles in aqueous media.

Preferable gases include those selected from the group consisting of air, noble gases, such as helium, neon, argon and xenon, carbon dioxide, nitrogen, fluorine, oxygen, sulfur-based gases, such as sulfur hexafluoride and sulfur tetrafluoride, fluorocarbons, perfluorocarbon gases, and mixtures thereof. Preferred gases are perfluorocarbon gases. Exemplary perfluorocarbon gases include, for example, perfluoromethane, perfluoroethane, perfluoropropane, perfluorobutane, perfluorocyclobutane and mixtures thereof. Also preferred are mixtures of different types of gases, such as a perfluorocarbon gas and another type of gas, such as oxygen. The gases discussed in Quay, published application WO 93/05819, including the high "Q" factor gases described therein, may be used also. The disclosures of Quay, published application WO 93/05819 are incorporated herein by reference in their entirety. In addition, paramagnetic gases and gases of isotopes, such as 170, may be used.

It is contemplated that contrast media which comprise these latter gases may also be used in connection with other diagnostic techniques, such as Magnetic Resonance Imaging (MRI).

Other gases, including the gases exemplified above, would be readily apparent to one skilled in the art based on the present disclosure.

In certain particularly preferred embodiments, a precursor to a gaseous substance is incorporated in the microspheres. Such precursors include materials which are capable of being converted to a gas in vivo. Exemplary precursors are materials which are liquids at room temperature and which, after being administered to a patient, undergo a phase transition to a gas in vivo. Preferably, the gaseous precursor is biocompatible, and the gas produced in vivo is biocompatible also. Exemplary of suitable gaseous precursors are of the perfluorocarbons. As the artisan will appreciate, a particular perfluorocarbon may exist in the liquid state when the microspheres are first made, and are thus used as a gaseous precursor, or the perfluorocarbon may be used directly as a gas. Whether the perfluorocarbon is used as a liquid or a gas generally depends on its liquid/gas phase transition temperature, or boiling point. For example, a preferred perfluorocarbon, perfluoropentane, has a liquid/gas phase transition temperature or boiling point of 29.5° C. This means that perfluoropentane will be a liquid at room temperature (about 25° C.), but will become a gas within the human body, the normal temperature of which (37° C.) is above the transition temperature or boiling point of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane is potentially useful as a gaseous precursor, although more likely as a gas, whereas perfluorohexane would likely be useful as a gaseous precursor only because of its relatively high boiling point.

A wide variety of materials can be used as gaseous precursors in the present compositions. It is only required that the material be capable of undergoing a phase transition to the gas phase upon passing through the appropriate temperature. Suitable gaseous precursors include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro- 1,3-butadiene, 2-methyl- 1,3-butadiene, hexafluoro-1,3-butadiene, butadiyne, 1-fluorobutane, 2-methylbutane, decafluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromo-butyraldehyde, carbonyl sulfide, crotononitrile, cyclobutane, methylcyclobutane, octafluorocyclobutane, perfluorocyclobutene, 3-chlorocyclopentene, perfluorocyclopentane, octafluorocyclopentene, cyclopropane, perfluorocyclopropane, 1,2-dimethyl-cyclopropane, 1,1-dimethylcyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis-(dimethylphosphine)amine, perfluorohexane, perfluoroheptane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1, 2,2-trifluoroethane, 1,1-dichloroethane, 1,1-dichloro-1,2,2, 2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, hexafluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neopentane, nitrous oxide, 1,2,3-nonadecane-tricarboxylic acid-2-hydroxytrimethylester, 1-nonene-3-yne, 1,4-pentadiene, n-pentane, perfluoropentane, 4-amino-4-methylpentan-2-one, 1-pentene, 2-pentene (cis), 2-pentene (trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3-dichloropropane, 1-chloropropane, chloropropane-(trans), 2-chloropropane, 3-fluoropropane, propyne, 3,3,3-trifluoropropyne, 3-fluorostyrene, sulfur (di)-decafluoride ($S_2F_{10}$), 2,4-diaminotoluene, trifluoroacetonitrile, trifluoromethyl peroxide, trifluoromethyl sulfide, tungsten hexafluoride, vinyl acetylene and vinyl ether.

In certain preferred embodiments, a gas, for example, air or a perfluorocarbon gas, is combined with a liquid perfluorocarbon, such as perfluorooctylbromide (PFOB), perfluorodecalin, perfluorododecalin, perfluorooctyliodide, perfluorotripropylamine, and perfluorotributylamine.

The size of the microspheres can be adjusted, if desired, by a variety of procedures including, for example, microemulsification, vortexing, extrusion, filtration, sonication, homogenization, repeated cycles of freezing and thawing cycles, extrusion under pressure through pores of defined size, and similar methods.

For intravascular use, the microspheres preferably have diameters of less than about 30 μm, and more preferably, less than about 12 μm. For targeted intravascular use including, for example, binding to certain tissue, such as cancerous tissue, the microspheres can be significantly smaller, for example, less than 100 nm in diameter. For enteric or gastrointestinal use, the microspheres can be significantly larger, for example, up to a millimeter in size. Preferably, the microspheres are sized to have diameters between about 20 μm and 100 μm.

Tabulated below is a listing of a series of gaseous precursors which undergo phase transitions from liquid to gas at relatively close to normal human body temperature (37°

C.) or below. Also listed in the table are the sizes, in diameter, of emulsified droplets that would be required to form a microsphere of a maximum size of about 10 μm.

TABLE 1

Physical Characteristics of Gaseous Precursors and Diameter of Emulsified Droplet to Form a 10 μm Microsphere

| Compound | Molecular Weight | Boiling Point (°C.) | Density | Diameter (μm) of emulsified droplet to make 10 micron microsphere |
|---|---|---|---|---|
| perfluoropentane | 288.04 | 29.5 | 1.7326 | 2.9 |
| 1-fluorobutane | 76.11 | 32.5 | 6.7789 | 1.2 |
| 2-methyl-butane (isopentane) | 72.15 | 27.8 | 0.6201 | 2.6 |
| 2-methyl-1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluorocyclobutane | 200.04 | −5.8 | 1.48 | 2.8 |
| decafluorobutane | 238.04 | −2 | 1.517 | 3.0 |
| hexafluoroethane | 138.01 | −78.1 | 1.607 | 2.7 |

*Source: Chemical Rubber Company Handbook of Chemistry and Physics Robert C. Weast and David R. Lide, eds. CRC Press, Inc. Boca Raton, Florida. (1989–1990).

It is part of the present invention to optimize the utility of the microspheres by using gases of limited solubility. Limited solubility, as used herein, refers to the ability of the gas to diffuse out of the microspheres by virtue of its solubility in the surrounding aqueous medium. A greater solubility in the aqueous medium imposes a gradient with the gas in the microsphere such that the gas will have a tendency to diffuse out of the microsphere. A lesser solubility in the aqueous medium will decrease the gradient between the microsphere and the interface such that the diffusion of the gas out of the microsphere will be impeded. Preferably, the gas entrapped in the microsphere has a solubility less than that of oxygen, namely, 1 part gas in 32 parts water. See *Matheson Gas Data Book*, Matheson Company, Inc. (1966). More preferably, the gas entrapped in the microsphere possesses a solubility in water less than that of air; and even more preferably, the gas entrapped in the microsphere possesses a solubility in water less than that of nitrogen.

Stabilizing Compounds

One or more stabilizing compounds are employed to form the microspheres, and to assure continued encapsulation of the gases or gaseous precursors. Even for relatively insoluble, non-diffusible gases, such as perfluoropropane or sulfur hexafluoride, improved microsphere preparations are obtained when one or more stabilizing compounds are utilized in the formation of the gas and gaseous precursor filled microspheres. These compounds maintain the stability and the integrity of the microspheres with regard to their size, shape and/or other attributes.

A wide variety of stabilizing compounds can be employed in the contrast media of the present invention. When combined with a gas and/or a gaseous precursor, the stabilizing compounds are capable of promoting the formation, and improving the stability, of the microspheres. The stabilized microspheres of the present invention are substantially resistant to degradation as measured by the loss of microsphere structure or encapsulated gas or gaseous precursor for a useful period of time. Typically, the microspheres are capable of retaining at least about 90 percent by volume of its original structure for a period of at least about two or three weeks under normal ambient conditions, although it is preferred that this period be at least about a month, more preferably, at least about two months, even more preferably, at least about six months, and more preferably, about a year, and still more preferably about three years. Thus, the microspheres of the present invention possess long shelf-lives, even under adverse conditions, including elevated temperatures and pressures.

The stability of the microspheres of the present invention is attributable, at least in part, to the materials from which the microspheres are made, and it is often not necessary to employ additional stabilizing additives, although it is optional, and sometimes preferred, to do so. Such additional stabilizing agents and their characteristics are explained in more detail below.

In preferred embodiments, the stabilizing compounds comprise biocompatible lipid compounds and/or polymeric compounds, with lipids being preferred. Preferably, the lipids or polymers are inert. Because of the ease of formulation, including the ability of producing the microspheres just prior to administration, the microspheres can be made conveniently on site.

Biocompatible Lipids

A wide variety of biocompatible lipids can be used as the stabilizing compound. Suitable lipids include, for example, lysolipids, phospholipids, such as phosphatidylcholines with both saturated and unsaturated lipids including dioleoylphosphatidylcholine, dimyristoylphosphatidylcholine, dipentadecanoylphosphatidylcholine, dilauroylphosphatidylcholine, dipalmitoylphosphatidylcholine (DPPC) and distearoylphosphatidylcholine (DSPC); phosphatidylethanolamines, such as dioleoylphosphatidylethanolamine, distearoylphosphatidylethanolamine and dipalmitoylphosphatidylethanolamine; phosphatidylserines; phosphatidylglycerols; phosphatidylinositols; sphingolipids, such as sphingomyelin; glycolipids, such as ganglioside GM1 and GM2; glucolipids; sulfatides; glycosphingolipids; phosphatidic acid; palmitic acid; stearic acid; arachidonic acid; oleic acid; lipids bearing polymers, including such polymers as polyethyleneglycol, chitin, hyaluronic acid or polyvinylpyrrolidone; lipids bearing sulfonated mono-, di-, oligo- or polysaccharides; cholesterols and cholesterol hemisuccinate; tocopherols and tocopherol hemisuccinate; lipids with ether and ester-linked fatty acids; polymerized lipids; diacetyl phosphate; dicetyl phosphate; stearylamine; cardiolipin; phospholipids with short chain fatty acids ($C_6$ to $C_8$); synthetic phospholipids with asymmetric acyl chains, for example, a first acyl chain of $C_6$ and a second acyl chain of $C_{12}$; ceramides; polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, sterols, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid, accharic acid, and polyuronic acid; saponins, including sarsasapogenin, smilagenin, hederagenin, oleanolic acid, and digitoxigenin; glycerol dilaurate, glycerol trilaurate, glycerol dipalmitate, glycerol and glycerol esters, including glycerol tripalmitate, glycerol distearate, glycerol tristearate, glycerol dimyristate, glycerol trimyristate; long chain alcohols of, for example, about 10 to about 30 carbon atoms, including n-decyl alcohol, lauryl alcohol, myristyl alcohol, cetyl alcohol, and n-octadecyl alcohol; alkyl phosphonates, alkyl phosphinates and alkyl phosphites; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy) hexyl-6-amino-6-deoxy-1-thio-α-D-mannopyranoside; 12-( ((7'-diethylaminocoumarin-3-yl)carbonyl)methylamino) octadecanoic acid; N-[12-(((7'-diethylaminocoumarin-3-yl) carbonyl)methylamino)octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine; and palmitoylhomocysteine.

Suitable lipid compounds include also lipids typically used to make mixed micelle systems, such as lauryltrimethylammonium bromide; cetyltrimethylammonium bromide; myristyltrimethylammonium bromide; alkyldimethylbenzylammonium chloride (where alkyl is, for example, $C_{12}$, $C_{14}$ or $C_{16}$); benzyldimethyldodecylammonium bromide/chloride; benzyldimethylhexadecylammonium bromide/chloride; benzyldimethyltetradecylammonium bromide/chloride; cetyldimethylethylammonium bromide/chloride; and cetylpyridinium bromide/chloride.

Suitable lipids for use in the present compositions include also lipids carrying a net charge, for example, anionic and/or cationic lipids. Exemplary cationic lipids include, for example, N-[1-(2,3-dioleoyloxy)propyl]-N,N,N-trimethylammonium chloride (DOTMA); 1,2-dioleoyloxy-3-(trimethylammonio)propane (DOTAP); 1,2-dioleoyl-e-(4'-trimethylammonio)butanoyl-sn-glycerol (DOTB); and lipids bearing cationic polymers, such as polylysine and polyarginine. In general the molar ratio of cationic lipid to non-cationic lipid in the microsphere may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the microsphere. Preferably, this non-cationic lipid is dipalmitoylphosphatidylcholine, dipalmitoylphosphatidylethanolamine or dioleoylphosphatidylethanolamine. In lieu of the cationic lipids as described above, lipids bearing cationic polymers, such as polylysine or polyarginine, as well as alkyl phosphates, alkyl phophinates, and alkyl phosphites, may also be used to construct the microspheres.

It has been surprisingly and unexpectedly found that the stability of the microspheres can be substantially improved by incorporating a small amount, for example, about 1 to about 10 mole percent of the total lipid, of a negatively charged lipid. It is believed that the negatively charged lipids enhance stability by reducing the tendency of the microspheres to rupture by fusing together. It is believed that this is achieved, at least in part, by the formation of a negatively charged layer from the negatively charged lipid on the outer surface of the microsphere. The negatively charged microsphere is then repulsed by other, similarly negatively charged microspheres. This repulsion prevents contact between microspheres which typically leads to a rupture of the walls of the microspheres and consolidation of the contacting microspheres into larger microspheres.

Suitable negatively charged lipids include, for example, lipids containing free carboxy ($CO_2^-$) groups, such as phosphatidylserine, phosphatidic acid, such as dipalmitoylphosphatidic acid, and fatty acids. In certain preferred embodiments, the lipid comprises dipalmitoylphosphatidylethanolamine and phosphatidic acid in a total amount of from about 0.5 to about 30 mole percent. In certain other preferred embodiments, the lipid comprises dipalmitoylphosphatidylcholine and distearoylphosphatidylcholine, in an amount of from about 70 to about 100 mole percent.

As noted above, it is desirable, in certain embodiments, to include as stabilizing compounds lipids bearing polymers. Preferably, the polymer is covalently bound to the lipid and has a molecular weight of from about 400 to about 100,000. Exemplary polymers include hydrophilic polymers, such as poly(ethyleneglycol) (PEG), poly(vinylpyrrolidine), polyoxomers and polysorbate and poly(vinylalcohol). Preferred among the PEG polymers are PEG 2000, PEG 5000 and PEG 8000, which have molecular weights of 2000, 5000 and 8,000 respectively. Other suitable polymers, hydrophilic and otherwise, will be readily apparent to those skilled in the art based on the present disclosure. Polymers which may be incorporated via alkylation or acylation reactions with a lipid are particularly useful for improving the stability of the lipid compositions. Exemplary lipids which bear hydrophilic polymers include, for example, dipalmitoylphosphatidylethanolamine-PEG, dioleoylphosphatidylethanolamine-PEG and distearylphosphatidylethanolamine-PEG.

In addition to, or instead of, the lipid compounds discussed above, the present lipid compositions may comprise an aliphatic carboxylic acid, for example, a fatty acid. Preferred fatty acids include those which contain about 5 to about 22 carbon atoms in the aliphatic group. The aliphatic group can be either linear or branched. Exemplary saturated fatty acids include, for example, (iso)lauric, (iso)myristic, (iso)palmitic and (iso)stearic acids. Exemplary unsaturated fatty acids include, for example, lauroleic, physeteric, myristoleic, palmitoleic, petroselinic, and oleic acid. Suitable fatty acids include also, for example, fatty acids in which the aliphatic group is an isoprenoid or prenyl group. In addition, carbohydrates bearing polymers may be used in the present lipid compositions. Carbohydrates bearing lipids are described, for example, in U.S. Pat. No. 4,310,505, the disclosures of which are hereby incorporated by reference herein, in their entirety.

Preferred lipids are phospholipids, including DPPC, DPPE, DPPA and DSPC, with DPPC being preferred.

Other lipid compounds for use in the present compositions, in addition to those exemplified above, would be apparent in view of the present disclosure. Preferably, lipids are selected to optimize certain desirable properties of the compositions, including stability and half-life. The selection of suitable lipids in the preparation of the present compositions, in addition to the lipids exemplified above, would be apparent to one skilled in the art and can be achieved without undue experimentation, based on the present disclosure.

As discussed in detail below, a wide variety of methods are available for the preparation of microspheres including, for example, shaking, drying, gas-installation, spray drying, and the like. Preferably, the microspheres are prepared from lipids which remain in the gel state, this being the temperature at which a lipid bilayer converts from the gel state to the liquid crystalline state. See, for example, Chapman et al., *J. Biol. Chem.* 1974 249, 2512–2521, the disclosures of which are hereby incorporated by reference herein, in their entirety. The following table lists representative lipids and their phase transition temperatures.

TABLE 2

Saturated Diacyl-sn-Glycero-3-Phosphocholines:
Main Chain Phase Transition Temperatures

| Carbons in Acyl Chains | Main Phase Transition Temperature °C. |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, e.g., Derek Marsh, *CRC Handbook of Lipid Bilayers*, p. 139 (CRC Press, Boca Raton, FL 1990).

The lipid material or other stabilizing compound used to form the microspheres is also preferably flexible, by which is meant, in the context of gas and gaseous precursor filled microspheres, the ability of a structure to alter its shape, for example, in order to pass through an opening having a size smaller than the microsphere.

Biocompatible Polymers

As noted above, the stabilizing compound can also comprise a biocompatible polymeric compound. The polymers can be naturally-occurring, semi-synthetic or synthetic. Exemplary natural polymers include, for example, polysaccharides, such as arabinans, fructans, fucans, galactans, galacturonans, glucans, mannans, xylans (such as, for example, inulin), levan, fucoidan, carrageenan, galactocarolose, pectic acid, amylose, pullulan, glycogen, amylopectin, cellulose, dextran, pustulan, chitin, agarose, keratin, chondroitan, dermatan, hyaluronic acid, alginic acid, xanthan gum, starch and various other natural homopolymer or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof.

Exemplary semi-synthetic polymers include carboxymethylcellulose, hydroxymethylcellulose, hydroxypropylmethylcellulose, methylcellulose, and methoxycellulose.

Exemplary synthetic polymers include polyethylenes, such as, for example, polyethylene glycol, polyoxyethylene, and polyethylene terephthlate, polypropylenes such as, for example, polypropylene glycol, polyurethanes, such as, for example, polyvinyl alcohol (PVA), polyvinylchloride and polyvinylpyrrolidone, polyamides, such as, for example, nylon, polystyrene, polylactic acids, fluorinated hydrocarbons, such as, for example, polytetrafluoroethylene, and polymethylmethacrylate, and derivatives thereof. Methods for the preparation of polymer-based microspheres will be readily apparent to those skilled in the art, once armed with the present disclosure, and when coupled with information known in the art, such as the information set forth in Unger, U.S. Pat. No. 5,205,290, the disclosures of which are hereby incorporated by reference herein in their entirety.

Preferably, the polymer possesses a relatively high water binding capacity. When used, for example, in the GI region, a polymer having a high water binding capacity can bind large amounts of free water. This enables the polymer to carry a large volume of liquid through the GI tract, thereby filling and distending the tract. The filled and distended GI tract permits enhanced CT imaging of the region.

In addition, where imaging of the GI region is desired, the polymer is preferably not substantially degraded in, and absorbed from, the GI region. Thus, metabolism and absorption within the GI tract is preferably minimized to avoid removal of the contrast agent. This also avoids the possible formation of gas within the GI tract from such degradation. For imaging the GI region, preferred polymers are capable of displacing air and minimizing the formation of large air bubbles within the contrast medium.

Particularly preferred embodiments of the present invention include microspheres wherein the stabilizing compound from which the stabilized gas and gaseous precursor filled microspheres are formed comprises three components: (1) a neutral lipid, for example, a nonionic or zwitterionic lipid, (2) a negatively charged lipid, and (3) a lipid bearing a hydrophilic polymer. Preferably, the amount of the negatively charged lipid will be greater than 1 mole percent of total lipid present, and the amount of lipid bearing a hydrophilic polymer will be greater than 1 mole percent of total lipid present. It is also preferred that the negatively charged lipid be a phosphatidic acid. The lipid bearing a hydrophilic polymer will desirably be a lipid covalently bound to the polymer and the polymer will preferably have a weight average molecular weight of from about 400 to about 100,000. The hydrophilic polymer is preferably selected from the group consisting of polyethyleneglycol (PEG), polypropyleneglycol, polyvinylalcohol, and polyvinylpyrrolidone and copolymers thereof. The PEG or other polymer may be bound to a lipid, for example, DPPE, through a covalent linkage, such as through an amide, carbamate or amine linkage. Alternatively, ester, ether, thioester, thioamide or disulfide (thioester) linkages may be used with the PEG or other polymer to bind the polymer to, for example, cholesterol or other phospholipids. Where the hydrophilic polymer is PEG, a lipid bearing such a polymer can be referred to as being "PEGylated". The lipid bearing a hydrophilic polymer is preferably dipalmitoylphosphatidylethanolamine-PEG 5000 (DPPE-PEG 5000), which means a dipalmitoylphosphatidylethanolamine lipid having a PEG polymer of a mean average molecular weight of about 5000 attached thereto.

Preferred embodiments of the present invention include microspheres which comprise, for example, about 77.5 mole percent dipalmitoylphosphatidylcholine (DPPC), about 12.5 mole percent of dipalmitoylphosphatidic acid (DPPA), and about 10 mole percent of dipalmitoylphosphatidylethanolamine-PEG 5000. Such compositions, in a ratio of mole percentages of 82:10:8 are preferred also. The DPPC component is zwitterionic and therefore, effectively neutral, since the phosphatidyl portion is negatively charged and the choline portion is positively charged. The DPPA component, which is negatively charged, is added to enhance stabilization in accordance with the mechanism described above regarding negatively charged lipids. The third component, DPPE-PEG 5000, provides a PEGylated material bound to the lipid membrane or skin of the microsphere by the DPPE moiety, with the PEG moiety free to surround the microsphere membrane or skin, and thereby form a physical barrier to various enzymatic and other endogenous agents in the body whose function is to degrade such foreign materials. It is also theorized that the PEGylated material is able to defeat the action of the macrophages of the human immune system, which would otherwise tend to surround and remove the foreign object. The result is an increase in the time during which the stabilized microspheres can exist, in vivo, and therefore function as CT contrast agents.

Auxiliary Stabilizing Compounds

It is also contemplated to be a part of the present invention to prepare stabilized gas and gaseous precursor filled microspheres using materials in addition to the biocompatible lipids and polymers described above, provided that the microspheres so prepared meet stability and other criteria set forth herein. These materials may be basic and fundamental and thus, can form the primary basis for creating or establishing the stabilized gas and gaseous precursor filled microspheres. On the other hand, they may be auxiliary, and therefore act as subsidiary or supplementary agents which either enhance the functioning of the basic stabilizing compound or compounds, or else contribute some desired property in addition to that afforded by the basic stabilizing compound.

However, it is contemplated that difficulty may be encountered in determining whether a particular compound is a basic or an auxiliary agent, since the functioning of the compound in question is generally determined empirically, or by the results produced with respect to producing stabilized microspheres. For example, the simple combination of a biocompatible lipid and water or saline, when shaken, will often give a cloudy solution subsequent to autoclaving for sterilization. Such a cloudy solution may function as a contrast agent, but is aesthetically objectionable and may imply instability in the form of undissolved or undispersed lipid particles. Thus, propylene glycol may be added to remove this cloudiness by facilitating dispersion or dissolution of the lipid particles. The propylene glycol may also function as a thickening agent which improves microsphere formation and stabilization by increasing the surface tension on the microsphere membrane or skin. It is possible that the propylene glycol further functions as an additional layer that coats the membrane or skin of the microsphere, thus providing additional stabilization.

Basic and auxiliary materials for use in the preparation of stabilized microspheres would be apparent to one skilled in the art based on the present disclosure. Such materials include conventional surfactants which are disclosed, for example, in D'Arrigo, U.S. Pat. Nos. 4,684,479 and 5,215,680, the disclosures of which are incorporated herein by reference, in their entirety.

Additional auxiliary and basic stabilizing compounds include such agents as oils, for example, peanut oil, canola oil, olive oil, safflower oil, corn oil, or any other oil which is commonly known to be ingestible. Another auxiliary and basic stabilizing compound is trehalose.

It has been found that the gas and gaseous precursor filled microspheres used in the present invention may be controlled according to size, solubility and heat stability by choosing from among the various additional or auxiliary stabilizing agents described herein. These agents can affect these parameters of the microspheres not only by their physical interaction with the lipid coatings, but also by their ability to modify the viscosity and surface tension of the surface of the gas and gaseous precursor filled microspheres. Accordingly, the gas and gaseous precursor filled microspheres may be favorably modified and further stabilized, for example, by the addition of a viscosity modifier, including, for example, carbohydrates and the phosphorylated and sulfonated derivatives thereof, polyethers, including polyethers having a molecular weight of, for example, from about 400 to about 100,000 and di- and trihydroxy alkanes and their polymers having a molecular weight of, for example, about 200 to about 50,000; emulsifying and/or solubilizing agents, including, for example, acacia, cholesterol, diethanolamine, glycerol monostearate, lanolin alcohols, lecithin, mono- and diglycerides, monoethanolamine, oleic acid, oleyl alcohol, poloxamer, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, and emulsifying wax; suspending and/or viscosity-increasing agents, including, for example, agar, alginic acid, aluminum monostearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropylmethylcellulose, magnesium-aluminum-silicate, methylcellulose, pectin, polyethylene oxide, povidone, propylene glycol alginate, silicon dioxide, sodium alginate, tragacanth, xanthan gum, α-d-gluconolactone, glycerol and mannitol; synthetic suspending agents, including, for example, polyethyleneglycol (PEG), polyvinylpyrrolidone (PVP), polyvinylalcohol (PVA), polypropylene glycol and polysorbate; and materials which raise the tonicity of the compositions, including, for example, sorbitol, propyleneglycol and glycerol.

Aqueous Diluents

As mentioned earlier, where the microspheres are lipid in nature, a particularly desired component of the stabilized microspheres is an aqueous environment of some kind, which induces the lipid, because of its hydrophobic/hydrophilic nature, to form microspheres, which is a highly stable configuration in such an environment. The diluents which can be employed to create such an aqueous environment include, but are not limited to, water, either deionized or containing any number of dissolved salts which will not interfere with the creation and maintenance of the stabilized microspheres or their use as CT agents, and normal saline and physiological saline.

Methods of Preparation

The stabilized gas and gaseous precursor filled microspheres used in the present invention may be prepared by a number of suitable methods. These are described below separately for gas filled microspheres, gaseous precursor filled microspheres, and both gas and gaseous precursor filled microspheres.

Methods of Preparation Using a Gas

A preferred embodiment comprises the steps of agitating an aqueous solution containing a stabilizing compound, preferably a lipid, in the presence of a gas at a temperature below the gel to liquid crystalline phase transition temperature of the lipid to form gas filled microspheres. The term agitating, and variations thereof, as used herein, means any motion that shakes an aqueous solution such that gas is introduced from the local ambient environment into the aqueous solution. The shaking must be of sufficient force to result in the formation of microspheres, particularly stabilized microspheres. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

Further, the shaking may occur manually or by machine. Mechanical shakers that may be used include, for example, a shaker table such as a VWR Scientific (Cerritos, Calif.) shaker table, or a Wig-L-Bug™ Shaker from Dental Mfg. Ltd., Lyons, Ill., which has been found to give excellent results. It is a preferred embodiment of the present invention that certain modes of shaking or vortexing be used to make stable microspheres within a preferred size range. Shaking is preferred, and it is preferred that this shaking be carried out using the Wig-L-Bug™ mechanical shaker. In accordance with this preferred method, it is preferred that a reciprocating motion be utilized to generate the gas and gaseous precursor filled microspheres. It is even more preferred that the motion be reciprocating in the form of an arc. It is still more preferred that the motion be reciprocating in the form of an arc between about 2° and about 20°, and yet further preferred that the arc be between about 5° and about 8°. It is most preferred that the motion is reciprocating between about 6° and about 7°, most particularly about 6.5°. It is contemplated that the rate of reciprocation, as well as the arc thereof, is particularly important in determining the amount and size of the gas filled microspheres formed. Preferably, the number of reciprocations or full cycle oscillations, is from about 1000 to about 20,000 per minute. More preferably, the number of reciprocations or oscillations is from about 5000 to about 8000. The Wig-L-Bug™, referred to above, is a mechanical shaker which provides 2000 pestle strikes every 10 seconds, i.e., 6000 oscillations every minute. Of course, the number of oscillations is dependent upon the mass of the contents being agitated, with the larger the mass, the fewer the number of oscillations. Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at about 60 to 300 revolutions per minute is more preferred. Vortexing at about 300 to 1800 revolutions per minute is even more preferred.

The formation of gas filled microspheres upon shaking can be detected visually. The concentration of lipid required to form a desired stabilized microsphere level will vary depending upon the type of lipid used, and may be readily determined by routine experimentation. For example, in preferred embodiments, the concentration of 1,2-dipalmitoylphosphatidylcholine (DPPC) used to form stabilized microspheres according to the methods of the present invention is about 0.1 mg/ml to about 30 mg/ml of saline solution, more preferably from about 0.5 mg/ml to about 20 mg/ml of saline solution, and even more preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and even more preferably from about 1 mg/ml to about 10 mg/ml of saline solution.

In addition to the simple shaking methods described above, more elaborate methods can also be employed. Such elaborate methods include, for example, liquid crystalline shaking gas instillation processes and vacuum drying gas instillation processes, such as those described in copending U.S. application Ser. No. 08/076,250, filed Jun. 11, 1993, which is incorporated herein by reference, in its entirety. When such processes are used, the stabilized microspheres which are to be gas filled, may be prepared prior to gas installation using any one of a variety of conventional liposome preparatory techniques which will be apparent to those skilled in the art. These techniques include freeze-thaw, as well as techniques such as sonication, chelate dialysis, homogenization, solvent infusion, microemulsification, spontaneous formation, solvent vaporization, French pressure cell technique, controlled detergent dialysis, and others, each involving preparing the microspheres in various fashions. See, e.g., Madden et al., *Chemistry and Physics of Lipids*, 1990 53, 37–46, the disclosures of which are hereby incorporated herein by reference in their entirety.

The gas filled microspheres prepared in accordance with the methods described above range in size from below a micron to over 100 µm in size. In addition, it will be noted that after the extrusion and sterilization procedures, the agitation or shaking step yields gas and gaseous precursor filled microspheres with substantially no or minimal residual anhydrous lipid phase in the remainder of the solution. (Bangham, A. D., Standish, M. M, & Watkins, J. C. (1965) *J. Mol. Biol.* Vol. 13, pp. 238–252 (1965). The resulting gas filled microspheres remain stable on storage at room temperature for a year or even longer.

The size of gas filled microspheres can be adjusted, if desired, by a variety of procedures, including microemulsification, vortexing, extrusion, filtration, sonication, homogenization, repeated freezing and thawing cycles, extrusion under pressure through pores of defined size, and similar methods. It may also be desirable to use the microspheres of the present invention as they are formed, without any attempt at further modification of the size thereof.

The gas filled microspheres may be sized by a simple process of extrusion through filters; the filter pore sizes control the size distribution of the resulting gas filled microspheres. By using two or more cascaded or stacked set of filters, for example, a 10 µm filter followed by an 8 µm filter, the gas filled microspheres can be selected to have a very narrow size distribution around 7 to 9 µm. After filtration, these stabilized gas filled microspheres remain stable for over 24 hours.

The sizing or filtration step may be accomplished by the use of a filter assembly when the suspension is removed from a sterile vial prior to use, or more preferably, the filter assembly may be incorporated into the syringe itself during use. The method of sizing the microspheres will then comprise using a syringe comprising a barrel, at least one filter, and a needle; and will be carried out by a step of extracting which comprises extruding said microspheres from said barrel through said filter fitted to said syringe between said barrel and said needle, thereby sizing said microspheres before they are administered to a patient in the course of using the microspheres as CT contrast agents in accordance with the present invention. The step of extracting may also comprise drawing said microspheres into said syringe, where the filter will function in the same way to size the microspheres upon entrance into the syringe. Another alternative is to fill such a syringe with microspheres which have already been sized by some other means, in which case the filter now functions to ensure that only microspheres within the desired size range, or of the desired maximum size, are subsequently administered by extrusion from the syringe.

In preferred embodiments, the solution or suspension of microspheres is extruded through a filter and is heat sterilized prior to shaking. Once gas filled microspheres are formed, they may be filtered for sizing as described above. These steps prior to the formation of gas and gaseous precursor filled microspheres provide the advantages, for example, of reducing the amount of unhydrated stabilizing compound, and thus providing a significantly higher yield of gas filled microspheres, as well as and providing sterile gas filled microspheres ready for administration to a patient. For example, a mixing vessel such as a vial or syringe may be filled with a filtered stabilizing compound, especially lipid suspension, and the suspension may then be sterilized within the mixing vessel, for example, by autoclaving. Gas may be instilled into the lipid suspension to form gas filled microspheres by shaking the sterile vessel. Preferably, the sterile vessel is equipped with a filter positioned such that the gas filled microspheres pass through the filter before contacting a patient.

The first step of this preferred method, extruding the solution of stabilizing compound through a filter, decreases the amount of unhydrated compound by breaking up the dried compound and exposing a greater surface area for hydration. Preferably, the filter has a pore size of about 0.1 to about 5 $\mu$m, more preferably, about 0.1 to about 4 $\mu$m, even more preferably, about 0.1 to about 2 $\mu$m, and still more preferably, about 1 $\mu$m. Unhydrated compound, especially lipid, appears as amorphous clumps of non-uniform size and is undesirable.

The second step, sterilization, provides a composition that may be readily administered to a patient for CT imaging. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, alternatively, the first and second steps, as outlined above, may be reversed, or only one of the two steps can be used.

Where sterilization occurs by a process other than heat sterilization at a temperature which would cause rupture of the gas filled microspheres, sterilization may occur subsequent to the formation of the gas filled microspheres, and is preferred. For example, gamma radiation may be used before and/or after gas filled microspheres are formed.

Methods of Preparation Using a Gaseous Precursor

In addition to the aforementioned embodiments, one can also use gaseous precursors contained in the microspheres which, upon activation, for example, by temperature, light, or pH, or other properties of the tissues of a host to which it is administered, undergo a phase transition from a liquid entrapped in the microspheres, to a gaseous state, expanding to create the stabilized, gas-filled microspheres of the present invention. This technique is described in detail in copending patent applications Ser. Nos. 08/160,232, filed Nov. 30, 1993 and 08/159,687, filed Nov. 30, 1993 both of which are incorporated herein by reference in their entirety.

The preferred method of activating the gaseous precursor is by exposure to elevated temperature. Activation or transition temperature, and like terms, refer to the boiling point of the gaseous precursor which is the temperature at which the liquid to gaseous phase transition of the gaseous precursor takes place. Useful gaseous precursors are those materials which have boiling points in the range of about −100° C. to 70° C. The activation temperature is particular to each gaseous precursor. An activation temperature of about 37° C., or about human body temperature, is preferred for gaseous precursors of the present invention. Thus, in preferred form, a liquid gaseous precursor is activated to become a gas at 37° C. However, the gaseous precursor may be in liquid or gaseous phase for use in the methods of the present invention.

The methods of preparing the CT imaging contrast agents of the present invention may be carried out below the boiling point of the gaseous precursor such that a liquid is incorporated into a microsphere. In addition, the methods may be performed at the boiling point of the gaseous precursor such that a gas is incorporated into a microsphere. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor-filled microspheres may be carried out at a temperature below the boiling point of the gaseous precursor. In this embodiment, the gaseous precursor is entrapped within a microsphere such that the phase transition does not occur during manufacture. Instead, the gaseous precursor-filled microspheres are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the microspheres upon attaining the gaseous state may be determined.

Alternatively, the gaseous precursors may be utilized to create stable gas-filled microspheres which are pre-formed prior to use. In this embodiment, the gaseous precursor is added to a container housing a suspending and/or stabilizing medium at a temperature below the liquid-gaseous phase transition temperature of the respective gaseous precursor.

As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas-filled spheres which entrap the gas of the gaseous precursor, ambient gas (e.g. air), or coentrap gas state gaseous precursor and ambient air. This phase transition can be used for optimal mixing and stabilization of the CT imaging contrast medium. For example, the gaseous precursor, perfluorobutane, can be entrapped in the biocompatible stabilizing compound, and as the temperature is raised, beyond 4° C., which is the boiling point of perfluorobutane, perfluorobutane gas is entrapped in microspheres. As an additional example, the gaseous precursor fluorobutane can be suspended in an aqueous suspension containing emulsifying and stabilizing agents, such as glycerol or propylene glycol, and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, stable gas-filled microspheres result.

Accordingly, the gaseous precursors may be selected to form a gas-filled microsphere in vivo or may be designed to produce the gas-filled microsphere in situ, during the manufacturing process, on storage, or at some time prior to use.

As a further embodiment of this invention, by preforming the gaseous precursor in the liquid state into an aqueous emulsion, the maximum size of the microbubble may be estimated by using the ideal gas law, once the transition to the gaseous state is effectuated. For the purpose of making gas-filled microspheres from gaseous precursors, the gas phase is assumed to form instantaneously and substantially no gas in the newly formed microsphere has been depleted due to diffusion into the liquid, which is generally aqueous in nature. Hence, from a known liquid volume in the emulsion, one would be able to predict an upper limit to the size of the gas-filled microsphere.

Pursuant to the present invention, an emulsion of a stabilizing compound such as a lipid, and a gaseous precursor, containing liquid droplets of defined size may be formulated, such that upon reaching a specific temperature, the boiling point of the gaseous precursor, the droplets will expand into gas-filled microspheres of defined size. The defined size represents an upper limit to the actual size because factors such as gas diffusion into solution, loss of gas to the atmosphere, and the effects of increased pressure are factors for which the ideal gas law cannot account.

The ideal gas law and the equation for calculating the increase in volume of the gas bubbles on transition from the liquid to gaseous states is as follows:

$$PV = nRT$$

where
P=pressure in atmospheres
V=volume in liters
n=moles of gas
T=temperature in °K
R=ideal gas constant=22.4 L atmospheres deg$^{-1}$ mole$^{-1}$ With knowledge of volume, density, and temperature of the liquid in the emulsion of liquids, the amount (e.g. number of moles) of liquid precursor as well as the volume of liquid precursor, a priori, may be calculated, which when converted to a gas, will expand into a microsphere of known volume. The calculated volume will reflect an upper limit to the size of the gas-filled microsphere, assuming instantaneous expansion into a gas-filled microsphere and negligible diffusion of the gas over the time of the expansion.

Thus, for stabilization of the precursor in the liquid state in an emulsion wherein the precursor droplet is spherical, the volume of the precursor droplet may be determined by the equation:

$$\text{Volume (sphere)} = 4/3\pi r^3$$

where
r=radius of the sphere

Thus, once the volume is predicted, and knowing the density of the liquid at the desired temperature, the amount of liquid (gaseous precursor) in the droplet may be determined. In more descriptive terms, the following can be applied:

$$V_{gas} = 4/3\pi (r_{gas})^3$$

by the ideal gas law, $$PV = nRT$$

substituting reveals, $$V_{gas} = nRT/P_{gas}$$

or, $$n = 4/3[\pi r_{gas}^3]P/RT \quad (A)$$

amount $n = 4/3[\pi r_{gas}^3 P/RT] \cdot MW_n$
Converting back to a liquid volume $$V_{liq} = [4/3[\pi r_{gas}^3]P/RT] \cdot MW_n/D] \quad (B)$$

where D=the density of the precursor
Solving for the diameter of the liquid droplet, $$\text{diameter}/2 = [3/4\pi[4/3 \cdot [\pi r_{gas}^3]P/RT]MW_n/D]^{1/3} \quad (C)$$

which reduces to $$\text{Diameter} = 2[[r_{gas}^3]P/RT[MW_n/D]]^{1/3}$$

As a further means of preparing microspheres of the desired size for use as CT imaging contrast agents in the present invention, and with a knowledge of the volume and especially the radius of the stabilizing compound/precursor liquid droplets, one can use appropriately sized filters in order to size the gaseous precursor droplets to the appropriate diameter sphere.

A representative gaseous precursor may be used to form a microsphere of defined size, for example, 10 μm diameter. In this example, the microsphere is formed in the bloodstream of a human being, thus the typical temperature would be 37° C. or 310 K. At a pressure of 1 atmosphere and using the equation in (A), 7.54 x 10$^{-17}$ moles of gaseous precursor would be required to fill the volume of a 10 μm diameter microsphere.

Using the above calculated amount of gaseous precursor, and 1-fluorobutane, which possesses a molecular weight of 76.11, a boiling point of 32.5° C. and a density of 0.7789 grams/mL$^{-1}$ at 20° C., further calculations predict that 5.74×10$^{-15}$ grams of this precursor would be required for a 10 μm microsphere. Extrapolating further, and armed with the knowledge of the density, equation (B) further predicts that $8.47 \times 10^{-16}$ mL of liquid precursor are necessary to form a microsphere with an upper limit of 10 μm.

Finally, using equation (C), an emulsion of lipid droplets with a radius of 0.0272 μm or a corresponding diameter of 0.0544 μm need be formed to make a gaseous precursor filled microsphere with an upper limit of a 10 μm microsphere.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas-filled microspheres used as CT imaging contrast agents in the methods of the present invention may be applied to all gaseous precursors activated by temperature. In fact, depression of the freezing point of the solvent system allows the use gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers for example, the freezing point is lowered by an amount that is dependent upon the composition of the solution. Thus, as defined by Wall, one can express the freezing point depression of the solvent by the following equation:

$$Inx_a=In(1-xb)=\Delta H_{fus}/R(1/T_o-1/T$$

where:

$x_a$=mole fraction of the solvent $x_b$=mole fraction of the solute $\Delta H_{fus}$=heat of fusion of the solvent $T_o$=Normal freezing point of the solvent The normal freezing point of the solvent results from solving the equation. If $x_b$ is small relative to $x_a$, then the above equation may be rewritten:

$$x^b=\Delta H_{fus}/R[T-T_o/T_oT]\approx\Delta H_{fus}\Delta T/RT_o^2$$

The above equation assumes the change in temperature AT is small compared to $T_2$. The above equation can be simplified further assuming the concentration of the solute (in moles per thousand grams of solvent) can be expressed in terms of the molality, m. Thus, $$X_b=m/[m+1000/m_a]\approx mMa/1000$$

where:

Ma=Molecular weight of the solvent, and m=molality of the solute in moles per 1000 grams.

Thus, substituting for the fraction $x_b$:

$$\Delta T=[M_aRT_o^{2/}1000\Delta H_{fus}]m$$

or $\Delta T=K_fm$, where $$K_f=M_aRT_o^2/1000\Delta H_{fus}$$

$K_f$ is referred to as the molal freezing point and is equal to 1.86 degrees per unit of molal concentration for water at one atmosphere pressure. The above equation may be used to accurately determine the molal freezing point of gaseous-precursor filled microsphere solutions used in the present invention.

Hence, the above equation can be applied to estimate freezing point depressions and to determine the appropriate concentrations of liquid or solid solute necessary to depress the solvent freezing temperature to an appropriate value.

Methods of preparing the temperature activated gaseous precursor-filled microspheres include:

(a) vortexing an aqueous suspension of gaseous precursor-filled microspheres used in the present invention; variations on this method include optionally autoclaving before shaking, optionally heating an aqueous suspension of gaseous precursor and lipid, optionally venting the vessel containing the suspension, optionally shaking or permitting the gaseous precursor microspheres to form spontaneously and cooling down the gaseous precursor filled microsphere suspension, and optionally extruding an aqueous suspension of gaseous precursor and lipid through a filter of about 0.22 $\mu$m, alternatively, filtering may be performed during in vivo administration of the resulting microspheres such that a filter of about 0.22 $\mu$m is employed;

(b) a microemulsification method whereby an aqueous suspension of gaseous precursor-filled microspheres of the present invention is emulsified by agitation and heated to form microspheres prior to administration to a patient; and (c) forming a gaseous precursor in lipid suspension by heating, and/or agitation, whereby the less dense gaseous precursor-filled microspheres float to the top of the solution by expanding and displacing other microspheres in the vessel and venting the vessel to release air; and (d) in any of the above methods, utilizing a sealed vessel to hold the aqueous suspension of gaseous precursor and stabilizing compound such as biocompatible lipid, said suspension being maintained at a temperature below the phase transition temperature of the gaseous precursor, followed by autoclaving to move the temperature above the phase transition temperature, optionally with shaking, or permitting the gaseous precursor microspheres to form spontaneously, whereby the expanded gaseous precursor in the sealed vessel increases the pressure in said vessel, and cooling down the gas-filled microsphere suspension, after which shaking may also take place.

Freeze drying is useful to remove water and organic materials from the stabilizing compounds prior to the shaking gas instillation method. Drying-gas instillation methods may be used to remove water from microspheres. By pre-entrapping the gaseous precursor in the dried microspheres (i.e. prior to drying) after warming, the gaseous precursor may expand to fill the microsphere. Gaseous precursors can also be used to fill dried microspheres after they have been subjected to vacuum. As the dried microspheres are kept at a temperature below their gel state to liquid crystalline temperature, the drying chamber can be slowly filled with the gaseous precursor in its gaseous state, e.g. perfluorobutane can be used to fill dried microspheres composed of dipalmitoylphosphatidylcholine (DPPC) at temperatures between 4° C. (the boiling point of perfluorobutane) and below 40° C., the phase transition temperature of the biocompatible lipid. In this case, it would be most preferred to fill the microspheres at a temperature about 4° C. to about 5° C.

Preferred methods for preparing the temperature activated gaseous precursor-filled microspheres comprise shaking an aqueous solution having a stabilizing compound such as a biocompatible lipid in the presence of a gaseous precursor at a temperature below the gel state to liquid crystalline state phase transition temperature of the lipid, and below the liquid state to gas state phase transition temperature of the gaseous precursor. Heating of the mixture to a temperature above the liquid state to gas state phase transition temperature of the gaseous precursor then causes the precursor to expand. Heating is then discontinued, and the temperature of the mixture is then be allowed to drop below the liquid state to gas state phase transition temperature of the gaseous precursor. Shaking of the mixture may take place during the heating step, or subsequently after the mixture is allowed to cool.

The present invention also contemplates the use of a method for preparing gaseous precursor-filled microspheres comprising shaking an aqueous solution comprising a stabilizing compound such as a biocompatible lipid in the presence of a gaseous precursor, and separating the resulting gaseous precursor-filled microspheres for computed tomography imaging use. Microspheres prepared by the foregoing methods are referred to herein as gaseous precursor filled microspheres prepared by a gel state shaking gaseous precursor instillation method.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* 1978, 75, 4194–4198. In contrast, the microspheres made according to preferred embodiments described herein are gaseous precursor filled, which imparts greater flexibility, since gaseous precursors after gas formation are more compressible and compliant than an aqueous solution. Thus, the gaseous precursor filled microspheres may be utilized in biological systems when formed at a temperature below the phase transition temperature of the lipid, even though the gel phase is more rigid.

The methods contemplated by the present invention provide for shaking an aqueous solution comprising a stabilizing compound, such as a biocompatible lipid, in the presence of a temperature activated gaseous precursor. Shaking, as used herein, is defined as a motion that agitates an aqueous solution such that gaseous precursor is introduced from the local ambient environment into the aqueous solution. Any type of motion that agitates the aqueous solution and results in the introduction of gaseous precursor may be used for the shaking. The shaking must be of sufficient force to allow the formation of foam after a period of time. Preferably, the shaking is of sufficient force such that foam is formed within a short period of time, such as 30 minutes, and preferably within 20 minutes, and more preferably, within 10 minutes.

The shaking may be by microemulsifying, by microfluidizing, for example, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table, such as a VWR Scientific (Cerritos, Calif.) shaker table, a microfluidizer, Wig-L-Bug™ (Crescent Dental Manufacturing, Inc., Lyons, Ill.), which has been found to give particularly good results, and a mechanical paint mixer, as well as other known machines. Another means for producing shaking includes the action of gaseous precursor emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at least 1000 revolutions per minute, an example of vigorous shaking, is more preferred. Vortexing at 1800 revolutions per minute is most preferred.

The formation of gaseous precursor filled microspheres upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous lipid solution; more preferably, the final volume of the foam is at least about three times the initial volume of the aqueous solution; even more preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gaseous precursor-filled microspheres becomes sufficiently thick so that it no longer clings to the side walls as it is swirled. At this time, the foam may cause the solution containing the gaseous precursor-filled microspheres to raise to a level of 30 to 35 ml.

The concentration of stabilizing compound, especially lipid required to form a preferred foam level will vary depending upon the type of stabilizing compound such as biocompatible lipid used, and may be readily determined by one skilled in the art, once armed with the present disclosure. For example, in preferred embodiments, the concentration of 1,2-dipalmitoylphosphatidylcholine (DPPC) used to form gaseous precursor-filled microspheres according to methods contemplated by the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gaseous precursor volume four times greater than the suspension volume alone. DSPC in a concentration of 10 mg/ml, upon shaking, yields a total volume completely devoid of any liquid suspension volume and contains entirely foam.

It will be understood by one skilled in the art, once armed with the present disclosure, that the lipids and other stabilizing compounds used as starting materials, or the microsphere final products, may be manipulated prior and subsequent to being subjected to the methods contemplated by the present invention. For example, the stabilizing compound such as a biocompatible lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gaseous precursor-filled microspheres.

According to the methods contemplated by the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

As already described above in the section dealing with the stabilizing compound, the preferred methods contemplated by the present invention are carried out at a temperature below the gel state to liquid crystalline state phase transition temperature of the lipid employed. By "gel state to liquid crystalline state phase transition temperature", it is meant the temperature at which a lipid bilayer will convert from a gel state to a liquid crystalline state. See, for example, Chapman et al., *J. Biol. Chem.* 1974, 249, 2512–2521.

Hence, the stabilized microsphere precursors described above, can be used in the same manner as the other stabilized microspheres used in the present invention, once activated by application to the tissues of a host, where such factors as temperature or pH may be used to cause generation of the gas. It is preferred that this embodiment is one wherein the gaseous precursors undergo phase transitions from liquid to gaseous states at near the normal body temperature of said host, and are thereby activated by the temperature of said host tissues so as to undergo transition to the gaseous phase therein. More preferably still, this method is one wherein the host tissue is human tissue having a normal temperature of about 37° C., and wherein the gaseous precursors undergo phase transitions from liquid to gaseous states near 37° C.

All of the above embodiments involving preparations of the stabilized gas and gaseous precursor filled microspheres used in the present invention, may be sterilized by autoclave or sterile filtration if these processes are performed before either the gas instillation step or prior to temperature mediated gas conversion of the temperature sensitive gaseous precursors within the suspension. Alternatively, one or more anti-bactericidal agents and/or preservatives may be included in the formulation of the contrast medium, such as sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, e.g., intravascularly or intraperitonealy. The appropriate means of sterilization will be apparent to the artisan instructed by the present description of the stabilized gas and gaseous precursor filled microspheres and their use. The contrast medium is generally stored as an aqueous suspension but in the case of dried microspheres or dried lipidic spheres the contrast medium may be stored as a dried powder ready to be reconstituted prior to use.

Methods of Use

The novel stabilized gas and gaseous precursor filled microspheres, useful as contrast media in CT imaging, will be found to be suitable for use in all areas where computed tomography imaging is employed.

In accordance with the present invention there is provided a method of imaging a patient generally, and/or in specifically diagnosing the presence of diseased tissue in a patient. The imaging process of the present invention may be carried out by administering a contrast medium of the invention to a patient, and then scanning the patient using computed tomography imaging to obtain visible images of an internal region of a patient and/or of any diseased tissue in that region. By region of a patient, it is meant the whole patient or a particular area or portion of the patient. The contrast medium is particularly useful in providing images of the gastrointestinal region, but can also be employed more broadly such as in imaging the vasculature or in other ways as will be readily apparent to those skilled in the art. The phrase gastrointestinal region or gastrointestinal tract, as used herein, includes the region of a patient defined by the esophagus, stomach, small and large intestines and rectum. The phrase vasculature, as used herein, denotes the blood vessels in the body or in an organ or part of the body. The patient can be any type of mammal, but most preferably is a human.

As one skilled in the art would recognize, administration of the stabilized gas and gaseous precursor filled microspheres used in the present invention may be carried out in various fashions, such as intravascularly, orally, intrarectally, intravaginally, intravesicularly, intraperitoneally, intracochlearly, intragenitouterally, etc., using a variety of dosage forms. When the region to be scanned is the gastrointestinal region, administration of the contrast medium of the invention is preferably carried out orally or rectally. The useful dosage to be administered and the particular mode of administration will vary depending upon the age, weight and the particular mammal and region thereof to be scanned, and the particular contrast medium of the invention to be employed. Typically, dosage is initiated at lower levels and increased until the desired contrast enhancement is achieved. Various combinations of the stabilized gas and gaseous precursor filled microspheres may be used to alter properties such as the viscosity, osmolarity or palatability, in the case of orally administered materials. In carrying out the CT imaging method of the present invention, the contrast medium can be used alone, or in combination with diagnostic, therapeutic or other agents. Such other agents include excipients such as flavoring or coloring materials. The CT imaging techniques which are employed are conventional and are described, for example, in *Computed Body Tomography*, Lee, J. K. T., Sagel, S. S., and Stanley, R. J., eds., 1983, Ravens Press, New York, N.Y., especially the first two chapters thereof entitled "Physical Principles and Instrumentation", Ter-Pogossian, M. M., and "Techniques", Aronberg, D. J.

The routes of administration and areas of usefulness of the gas and gaseous precursor filled microspheres are not limited merely to the blood volume space, i.e., the vasculature. CT imaging can be achieved with the gas and gaseous precursor filled microspheres used in the present invention if the microspheres are ingested by mouth so as to image the gastrointestinal tract. Alternatively, rectal administration of these stabilized gas microspheres can result in excellent imaging of the lower gastrointestinal tract including the rectum, descending colon, transverse colon, and ascending colon, as well as the appendix. It may be possible to achieve imaging of the ileum, and conceivably the jejunum, by way of this rectal route. As well, direct intraperitoneal administration may be achieved to visualize the peritoneum. It is also contemplated that the stabilized gas and gaseous precursor filled microspheres may be administered directly into the ear canals such that one can visualize the canals as well as the Eustachian tubes and, if a perforation exists, the inner ear. It is also contemplated that the stabilized gas and gaseous precursor filled microspheres may be administered intranasally to aid in the visualization of the nasal septum as well as the nasal sinuses by computed tomography imaging.

Other routes of administration of the microsphere contrast agents of the present invention, and tissue areas whose imaging is enhanced thereby include, but are not limited to 1) intranasally for imaging the nasal passages and sinuses including the nasal region and sinuses and sinusoids; 2) intranasally and orally for imaging the remainder of the respiratory tract, including the trachea, bronchus, bronchioles, and lungs; 3) intracochlearly for imaging the hearing passages and Eustachian tubes, tympanic membranes and outer and inner ear and ear canals; 4) intraocularly for imaging the regions associated with vision; 5) intraperitoneally to visualize the peritoneum; and 6) intravesicularly, i.e., through the bladder, to image all regions of the genitourinary tract via the areas thereof, including, but not limited to, the urethra, bladder, ureters, kidneys and renal vasculature and beyond, e.g., to perform cystography or to confirm the presence of ureteral reflux.

The invention is further described in the following examples. All of the examples are actual examples. These examples are for illustrative purposes only, and are not to be construed as limiting the appended claims.

EXAMPLES

Various of the materials used in the following examples are commercially available. All of the lipids were purchased from Avanti Polar Lipids (Alabaster, Ala.). Perfluoropentane and perfluorohexane were purchased from PCR Chemicals, Inc. (Gainesville, Fla.).

In the following examples, "DPPE" refers to dipalmitoylphosphatidylethanolamine; "DPPA" refers to dipalmitoylphosphatidic acid; and "DPPC" refers to dipalmitoylphosphatidylcholine. "PEG 5000" refers to poly (ethylene glycol) polymer having a molecular weight of about 5000. "DPPE-PEG-5000" refers to DPPE which is covalently bound to PEG 5000.

Example 1

This example describes the preparation of gas and gas precursor filled microspheres within the scope of the invention.

DPPC (77.5 mole %), DPPA (12.5 mole %), and DPPE-PEG 5000 (10 mole %) were introduced into a carrier solution of normal saline with glycerol (10 wt. %) and propylene glycol (10 wt. %). To this mixture was added perfluoropentane and a portion of the suspension (6 mL) was placed in a 18 mL glass vial and autoclaved for 15 minutes at 121° C. The resulting translucent suspension was allowed to cool to room temperature. No appreciable foam could be seen was observed, but gentle shaking produced a few small bubbles at the top of the suspension. Shaking on a Wig-L-Bug™ (Crescent Dental Mfg. Corp., Lyons, Ill.) for 2 minutes resulted in a dense foam that substantially filled the entire volume of the vial.

Samples of the lipid/perfluoropentane (PFP) suspension, with and without shaking, were scanned by computed tomography using a Siemens DRH Somatom Ill (Siemens, Iselin, N.J.), at 125 peak kilovolts with 410 milliampseconds and an 8 millimeter slice thickness and a zoom factor of 1.4. The images processed with a window width of 380 Hounsefield Units (HU) and a center of 30 HU showed fluid density in the unshaken sample and complete blackness in the shaken sample. When examined with a window width of 1,500 HU and a center of –600 HU, which corresponds to window settings of the type used for lung scanning, the unshaken sample appeared bright white and the shaken sample was only faintly visible. The density of the samples was measured and the unshaken sample measured 84.2 HU (S.D. 38.02) and the shaken sample measured –548.3 HU±5.92 HU.

Example 2

This example is directed to an analysis the effect of manual and mechanical shaking on microsphere size.

A lipid/PFP suspension was prepared as described in Example 1. A sample of the suspension was shaken at room temperature manually (much less vigorously than with the Wig-L-Bug mechanical shaker utilized in Example 1). Substantially no foam was produced, only a few bubbles at the top of the liquid layer. However, when the sample was warmed to body temperature, 37° C., i.e., above the 27.5° C. boiling point of the perfluoropentane, and shaken manually, foam readily appeared and filled the entire vial. When the foam produced by the Wig-L-Bug mechanical shaker at room temperature was compared to the foam produced manually at body temperature, it was noted that the microspheres produced by manual shaking were somewhat larger than the microspheres produced by the Wig-L-Bug mechanical shaker. The microspheres produced by manual shaking rose to the surface more quickly than the microspheres produced by the Wig-L-Bug mechanical shaker, a further indication that the microspheres produced by mechanical shaking were smaller than the microspheres produced by manual shaking, since larger microspheres will rise more quickly.

Example 3

This example is directed to the formation of stabilized gas-filled microspheres comprising lipid bilayers with polyvinyl alcohol.

The effect of a polymer, namely, polyvinylalcohol, on the size of microspheres containing perfluorocarbons is illustrated in this example. Gas-filled microspheres comprising a lipid were prepared by the addition of 5 mg/mL of a suspension of DPPC:phosphatidic acid, and DPPE-PEG 5000 in a molar weight ratio of 82:8:10 in a vehicle containing 5% by weight of polyvinylalcohol (weight average M.W. 50,000, 99+% hydrolyzed) in normal saline. To this mixture was added 50 $\mu$L of perfluoropentane. An identical suspension to the above described suspension was also prepared except that the vehicle was normal saline, glycerol, and propylene glycol in a ratio of 8:1:1, v:v:v (Spectrum Chemical Co., Gardena, Calif.). The suspensions were then autoclaved at 121° C. for 21 minutes in a Barnstead/Thermolyne autoclave (Barnstead/Thermolyne, Rancho Dominguez, Calif.). The temperatures of the resultant products were then equilibrated to 30° C. in a VWR Model 2500 incubator (VWR Manufacturing Corp., Albuquerque, N.M.). The slightly opaque suspensions were then shaken on a Wig-L-Bug shaker (Crescent Dental Mfg. Corp., Lyons, Ill.) for two minutes. This led to the production of foams. The subsequent foam samples were then sized on a Particle Sizing Systems Model 770 light obscuration sizer. The instrument was calibrated with standard sized latex beads ranging in size from 2.02 $\mu$m to 41.55 $\mu$m (Coulter Electronics, Inc., Hialeah, Fla.). The sampling vehicle was deionized water. The size distributions of the PVA-containing sample vs. the normal saline, glycerol, propylene glycol sample were as follows:

TABLE 3

Sizing of Gas-Filled Microspheres Comprising Lipid Bilayers with and without Polyvinyl Alcohol (PVA)

|  | 5% PVA Sample | Normal Saline, Glycerol, Propylene Glycol Sample |
| --- | --- | --- |
| Average Size | 5.51 μm | 5,82 μm |
| 95% less than | 14.45 μm | 19.1 μm |
| 99.9% less than | 72.2 μm | 75.6 μm |

Example 4

This example describes the use of perfluoropentane in the preparation of microspheres comprising lipid bilayers.

In an 18 mL vial, 6 mL of a suspension of 5 mg/mL lipid consisting of 77.5 mole % 1,2 dipalmitoyl-3-sn glycerophosphatidylcholine (DPPC), 12.5 mole % phosphatidic acid, and 10 mole % 1,2 dipalmitoyl-3-sn-phosphatidylethanolamine-polyethyleneglycol 5000 (DPPE-PEG 5000) was added followed by the addition of 50 μL of perfluoropentane, injected into the solution at room temperature. The head space in the vial was filled with air at ambient pressure and the vial was sealed with a teflon stopper and aluminum seal (VWR, Albuquerque, N.M.). The vial was then autoclaved at 121° C. for 15 minutes (Barnstead Thermolyne, Dubuque, Iowa). A translucent homogeneous suspension resulted. The vial was then removed from the autoclave, allowed to cool to room temperature, and then shaken for two minutes on a Wig-L-Bug shaker (Crescent Dental Manufacturing Corp., Lyons, Ill.). The entire vial was then found to be filled with foam. The vial was thereafter placed in a refrigerator at 4° C. and the foam persisted. By comparison, foam prepared with air or nitrogen gas alone in the same mixture of lipids, i.e., without the addition of perfluoropentane, did not persist as long as the foam produced using perfluoropentane. The duration of the foam prepared with the mixture of perfluoropentane and air was surprising; particularly so when it is considered that the boiling point of perfluoropentane is approximately 27.5° C. Room temperature under the conditions of this experiment was about 20° C., and thus at 4° C. it would have expected that the foam would collapse. This experiment thus demonstrates the surprising discovery that the presence of perfluorocarbons, despite being in the liquid state, can contribute to stabilization of the foam.

Example 5

This example describes the use of perfluorohexane in the preparation of microspheres comprising lipid bilayers.

To further demonstrate that a liquid-state perfluorocarbon can contribute to stabilization of a gas-filled microsphere foam, the result obtained using perfluorohexane (b.p. 56° C.) was evaluated. A suspension of lipids was prepared as described above in Example 4, except that 50 μL of perfluorohexane was added to the vial in lieu of the perfluoropentane. The suspension was autoclaved yielding a translucent-to-cloudy suspension of lipids. The material was shaken on the Wig-L-Bug (Crescent Dental Mfg. Corp., Lyons, Ill.) for two minutes and a foam again resulted. The volume of foam was greater than the control sample, which utilized air alone as the ambient gas. Once again, the foam remained stable and persisted longer than the air sample. This clearly demonstrates that the presence of the perfluorohexane, which is liquid at human physiological temperatures, functions to stabilize a gas-filled microsphere foam.

Example 6

This example describes trehalose stabilization of gas-filled microspheres comprising lipid bilayers.

A gas-filled microsphere foam was prepared from a stabilizing compound vehicle comprising normal saline:glycerol:propylene glycol (8:1:1, v:v:v) with the lipids set forth in Example 4 above, and shaken as described therein on a Wig-L-Bug for two minutes, yielding approximately 6 mL of foam at room temperature. After four days, it was discovered that the foam was no longer present. When the above experiment was repeated with the same lipids, except that trehalose, D-glucopyranose, a disaccharide, was added in a 1:1 molar ratio of trehalose to lipid, the foam was found to persist longer than the control. Repeating the experiment yielded similar results. This experiment clearly demonstrates that trehalose can function as an auxiliary stabilizing compound to lengthen the time duration of gas-filled microspheres of the present invention.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

What is claimed is:

1. A method of providing an image of an internal region of a patient comprising (i) administering to the patient an aqueous composition which comprises gaseous precursor-filled lipid microspheres, (ii) allowing said gaseous precursor to undergo a phase transition from a liquid to a gas, and (iii) scanning the patient using computed tomography to obtain visible images of said region, wherein said gaseous precursor comprises a perfluorocarbon and said microspheres are formulated from one or more phospholipids which contain substantially no disulfide linkages.

2. A method for diagnosing the presence of diseased tissue in a patient comprising (i) administering to the patient an aqueous composition which comprises gaseous precursor-filled lipid microspheres, (ii) allowing said gaseous precursor to undergo a phase transition from a liquid to a gas, and (iii) scanning the patient using computed tomography to obtain visible images of any diseased tissue in the patient, wherein said gaseous precursor comprises a perfluorocarbon and said microspheres are formulated from one or more phospholipids which contain substantially no disulfide linkages.

3. A method according to claim 1 wherein said gaseous precursor undergoes a phase transition from liquid to gaseous states at near the normal body temperature of the patient.

4. A method according to claim 1 wherein said phospholipids are selected from the group consisting of phosphatidylcholine, phosphatidylethanolamine and phosphatidic acid.

5. A method according to claim 4 wherein said phosphatidylcholine is selected from the group consisting of dioleoylphosphatidylcholine, dimyristoylphosphatidylcholine, dipentadecanoylphosphatidylcholine, dilauroylphosphatidylcholine, dipalmitoylphosphatidylcholine and distearoylphosphatidylcholine.

6. A method according to claim 5 wherein said phosphatidylcholine comprises dipalmitoylphosphatidylcholine.

7. A method according to claim 4 wherein said phosphatidylethanolamine is selected from the group consisting of dipalmitoylphosphatidylethanolamine, distearoylphosphatidylethanolamine, dioleoylphosphatidylethanolamine, N-succinyldioleoylphosphatidylethanolamine and 1-hexadecyl-2-palmitoylglycerophosphoethanolamine.

8. A method according to claim 7 wherein said phosphatidylethanolamine comprises dipalmitoylphosphatidylethanolamine.

9. A method according to claim 4 wherein said phosphatidic acid comprises dipalmitoylphosphatidic acid.

10. A method according to claim 1 wherein said phospholipid further comprises a polymer.

11. A method agent according to claim 10 wherein said polymer comprises a hydrophilic polymer.

12. A method according to claim 11 wherein said hydrophilic polymer comprises polyethylene glycol.

13. A method according to claim 1 wherein said lipid comprises dipalmitoylphosphatidylethanolamine and phosphatidic acid in a combined amount of from about 0.5 to about 30 mole percent.

14. A method according to claim 1 wherein said phospholipid is selected from the group consisting of dipalmitoylphosphatidylcholine and distearoylphosphatidylcholine, in an amount of from about 70 to about 100 mole percent.

15. A method according to claim 1 wherein said phospholipid comprises: (i) a neutral phospholipid, (ii) a negatively charged phospholipid, and (iii) a phospholipid bearing a hydrophilic polymer; wherein the amount of said negatively charged phospholipid is greater than 1 mole percent of the total phospholipid present and the amount of phospholipid bearing a hydrophilic polymer is greater than 1 mole percent of the total phospholipid present.

16. A method according to claim 15 wherein said negatively charged phospholipid is phosphatidic acid and wherein the polymer in said phospholipid bearing a hydrophilic polymer has a weight average molecular weight of from about 400 to about 100,000 and is covalently bound to said phospholipid.

17. A method according to claim 16 wherein said hydrophilic polymer is selected from the group consisting of polyethyleneglycol, polypropyleneglycol, polyvinylalcohol and polyvinylpyrrolidone and copolymers thereof, and wherein said phospholipid of said phospholipid bearing a hydrophilic polymer is selected from the group consisting of dipalmitoylphosphatidylethanolamine and distearoylphosphatidylethanolamine.

18. A method according to claim 1 wherein said phospholipid comprises about 77.5 mole percent of dipalmitoylphosphatidylcholine, about 12.5 mole percent of dipalmitoylphosphatidic acid, and about 10 mole percent of dipalmitoylphosphatidylethanolamine-polyethyleneglycol 5000.

19. A method according to claim 1 wherein said phospholipid comprises about 82 mole percent of dipalmitoylphosphatidylcholine, about 10 mole percent of dipalmitoylphosphatidic acid, and about 8 mole percent of dipalmitoylphosphatidylethanolamine-polyethyleneglycol 5000.

20. A method according to claim 1 wherein said composition further comprises compounds selected from the group consisting of ingestible oils; mixed micelle systems compounds; viscosity modifiers; emulsifying and/or solubilizing agents; suspending or viscosity-increasing agents; synthetic suspending agents; and tonicity-raising agents.

21. A method according to claim 1 wherein said microspheres are prepared from a composition comprising dipalmitoylphosphatidylcholine, glycerol and propylene glycol.

22. A method according to claim 1 wherein said perfluorocarbon is selected from the group consisting of perfluoropropane, perfluorobutane, perfluorocyclobutane, perfluoropentane, perfluorohexane and perfluoroheptane.

23. A method according to claim 1 wherein said microspheres are selected from the group consisting of unilamellar microspheres, oligolamellar microspheres and multilamellar microspheres.

24. A method according to claim 23 wherein said microspheres comprise unilamellar microspheres.

25. A method according to claim 23 wherein said microspheres comprise a monolayer.

26. A method according to claim 25 wherein said gaseous precursor comprises a perfluorocarbon.

27. A method according to claim 26 wherein said perfluorocarbon is perfluoropropane.

28. A method according to claim 27 wherein said perfluorocarbon is perfluoropentane.

29. A method according to claim 23 wherein said microspheres comprise a bilayer.

30. A method according to claim 29 wherein said gaseous precursor comprises a perfluorocarbon.

31. A method according to claim 30 wherein said perfluorocarbon is perfluoropropane.

32. A method according to claim 30 wherein said perfluorocarbon is perfluoropentane.

33. A method according to claim 23 wherein said microspheres are selected from the group consisting of oligolamellar microspheres and multilamellar microspheres.

34. A method according to claim 33 wherein said microspheres comprise a monolayer.

35. A method according to claim 34 wherein said gaseous precursor comprises a perfluorocarbon.

36. A method according to claim 35 wherein said perfluorocarbon is perfluoropropane.

37. A method according to claim 35 wherein said perfluorocarbon is perfluoropentane.

38. A method according to claim 33 wherein said microspheres comprise a bilayer.

39. A method according to claim 38 wherein said gaseous precursor comprises a perfluorocarbon.

40. A method according to claim 39 wherein said perfluorocarbon is perfluoropropane.

41. A method according to claim 39 wherein said perfluorocarbon is perfluoropentane.

42. A method according to claim 1 wherein the region comprises the vasculature.

43. A method according to claim 1 wherein the region comprises the cardiovascular region.

44. A method according to claim 1 wherein the region comprises the gastrointestinal region.

45. A method according to claim 1 wherein said scanning is of a region of a patient selected from the group consisting of the intranasal tract, the auditory canal, the intraocular region, the intraperitoneal region, the kidneys, the urethra and the genitourinary tract.

46. A method according to claim 1 wherein said microspheres are rehydrated from lyophilized microspheres.

47. A method according to claim 22 wherein said gaseous precursor filled microspheres further comprise nitrogen.

48. A method according to claim 2 wherein said microspheres are rehydrated from lyophilized microspheres.

49. A method according to claim 2 wherein said gaseous precursor filled microspheres further comprise nitrogen in combination with said perfluorocarbon, wherein said perfluorocarbon is selected from the group consisting of perfluoromethane, perfluoroethane, perfluoropropane, perfluorobutane, perfluorocyclobutane, perfluoropentane, perfluorohexane, and perfluoroheptane.

50. A method according to claim 49 wherein said perfluorocarbon is perfluoropropane.

51. A method according to claim 49 wherein said perfluorocarbon is perfluorohexane.

* * * * *

UNITED STATES PATENT AND TRADEMARK OFFICE
CERTIFICATE OF CORRECTION

PATENT NO. : 5,874,062
DATED : February 23, 1999
INVENTOR(S) : Evan C. Unger

It is certified that error appears in the above-indentified patent and that said Letters Patent is hereby corrected as shown below:

On the cover page, first column, under "U.S. PATENT DOCUMENTS", at "3,293,114", please delete "Kenage et al." and insert --Kenaga et al.-- therefor.

On the cover page, first column, under "U.S. PATENT DOCUMENTS", please delete "4,331,657" and insert --4,331,654-- therefor.

On page 2, second column, under "U.S. PATENT DOCUMENTS", at "5,567,414", please delete "Schnider et al." and insert --Schneider et al.-- therefor.

On page 2, second column, under "FOREIGN PATENT DOCUMENTS", at "0 314 764 B1", please delete "3/1992" and insert --9/1992-- therefor.

On page 3, first column, under "OTHER PUBLICATIONS", at "Thanassi", second line thereof, please delete "5-Deoxypridoxal" and insert --5-Deoxypyridoxal-- therefor.

On page 3, first column, under "OTHER PUBLICATIONS", at "Stelmashok et al.", second line thereof, please delete "(1997)" and insert --(1977)-- therefor.

On page 4, first column, under "OTHER PUBLICATIONS", at "Fukuda et al.", second line thereof, please delete "Diotadecyldimethylammonium" and insert --Dioctadecyldimethylammonium-- therefor.

UNITED STATES PATENT AND TRADEMARK OFFICE
CERTIFICATE OF CORRECTION

PATENT NO. : 5,874,062
DATED : February 23, 1999
INVENTOR(S) : Evan C. Unger

It is certified that error appears in the above-indentified patent and that said Letters Patent is hereby corrected as shown below:

On page 4, first column, under "OTHER PUBLICATIONS", at the second occurrence of "Crowe et al.", please delete "*Biophysics*vol.", and insert --*Biophysics*, vol.-- therefor.

On page 4, first column, under "OTHER PUBLICATIONS", at "Shiina et al.", please delete "Hyperthermiaby" and insert --Hyperthermia by-- therefor.

On page 4, second column, under "OTHER PUBLICATIONS", at "Szoka et al.", please delete "Prepartion" and insert --Preparation-- therefor.

On page 4, second column, under "OTHER PUBLICATIONS", at "*Mammalian Cells*", please delete "*Cells*" and insert --*Cell*-- therefor.

On page 4, second column, under "OTHER PUBLICATIONS", at "Poznansky et al.", please delete "Biologica" and insert --Biological-- therefor.

On page 4, second column, under "OTHER PUBLICATIONS", at "Thompson", second line thereof, please delete "Phases" and insert --Phase-- therefor.

On page 5, second column, under "OTHER PUBLICATIONS", at "Ter-Pogossian", please delete "*Pronciples*" and insert --*Principles*-- therefor.

UNITED STATES PATENT AND TRADEMARK OFFICE
CERTIFICATE OF CORRECTION

PATENT NO. : 5,874,062
DATED : February 23, 1999
INVENTOR(S) : Evan C. Unger

It is certified that error appears in the above-indentified patent and that said Letters Patent is hereby corrected as shown below:

In column 8, line 67, please delete "170" and insert --$^{17}$O-- therefor.

In column 14, line 4, please delete "phophinates" and insert --phosphinates-- therefor.

In column 33, line 10, Table 3, please delete "5,82 $\mu$m" and insert --5.82 $\mu$m-- therefor.

In column 35, lines 10-11, claim 8, please delete "phoshpatidylethanolamine" and insert --phosphatidylethanolamine-- therefor.

In column 36, line 20, claim 28, please delete "claim 27" and insert --claim 26-- therefor.

Signed and Sealed this

Fourth Day of April, 2000

Attest:

Q. TODD DICKINSON

Attesting Officer

Director of Patents and Trademarks